United States Patent
Kai et al.

(10) Patent No.: US 8,389,131 B2
(45) Date of Patent: Mar. 5, 2013

(54) MATERIAL FOR USE IN PHOSPHORESCENT DEVICE AND ORGANIC ELECTROLUMINESCENT DEVICE USING SAME

(75) Inventors: Takahiro Kai, Kitakyushu (JP); Masaki Komori, Kitakyushu (JP); Toshihiro Yamamoto, Kitakyushu (JP); Megumi Matsumoto, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/255,193

(22) PCT Filed: Mar. 24, 2010

(86) PCT No.: PCT/JP2010/055115
§ 371 (c)(1),
(2), (4) Date: Sep. 7, 2011

(87) PCT Pub. No.: WO2010/113726
PCT Pub. Date: Oct. 7, 2010

(65) Prior Publication Data
US 2011/0315975 A1    Dec. 29, 2011

(30) Foreign Application Priority Data

Mar. 31, 2009  (JP) .................................. 2009-085709

(51) Int. Cl.
*H01L 51/50*    (2006.01)
(52) U.S. Cl. ........ 428/690; 428/917; 313/504; 313/505; 313/506; 257/40; 257/E51.05; 257/E51.026; 257/E51.032; 546/18; 546/79; 546/81; 546/101; 548/440
(58) Field of Classification Search .................. 428/690, 428/917; 313/504, 505, 506; 257/40, E51.05, 257/E51.026, E51.032; 546/18, 79, 81, 101; 548/440

See application file for complete search history.

(56) References Cited

U.S. PATENT DOCUMENTS

| | | | |
|---|---|---|---|
| 5,942,340 A | * | 8/1999 | Hu et al. ........................ 428/690 |
| 2008/0067924 A1 | * | 3/2008 | Prakash et al. ................. 313/504 |

(Continued)

FOREIGN PATENT DOCUMENTS

| WO | WO 2007/063754 A1 | 6/2007 |
|---|---|---|
| WO | WO 2008/056746 A1 | 5/2008 |
| WO | WO 2009/136596 A1 | 11/2009 |

OTHER PUBLICATIONS

English translation of International Preliminary Report on Patentability issued Nov. 17, 2011, in PCT International Application No. PCT/JP2010/055115.

*Primary Examiner* — Jennifer Chriss
*Assistant Examiner* — Gregory Clark
(74) *Attorney, Agent, or Firm* — Birch, Stewart, Kolasch & Birch, LLP

(57) ABSTRACT

Provided is an organic electroluminescent device (organic EL device), in which the luminous efficiency of the device is improved, driving stability is sufficiently ensured, and the construction of the device is simple. This organic EL device is an organic electroluminescent device, including a light-emitting layer between an anode and a cathode laminated on a substrate, in which the light-emitting layer contains a phosphorescent light-emitting dopant and an indolocarbazole compound as a host material. Examples of the indolocarbazole compound include a compound represented by the following formula (1). It should be noted that in the formulae: a ring A and a ring B are represented by the formulae (1a) and (1b), respectively; Ar's each represent an aromatic hydrocarbon group or an aromatic heterocyclic group; R's each represent a hydrogen atom, an alkyl group, or a cycloalkyl group; X represents a methine group or a nitrogen atom; A represents an aromatic hydrocarbon group, an alkyl group, a cycloalkyl group, or a group represented by the formula (1c); and n represents 0 or 1.

7 Claims, 3 Drawing Sheets

U.S. PATENT DOCUMENTS

2009/0302742 A1 12/2009 Komori et al.
2010/0187977 A1 7/2010 Kai et al.
2011/0062862 A1 3/2011 Yamamoto et al.

* cited by examiner

MATERIAL FOR USE IN PHOSPHORESCENT DEVICE AND ORGANIC ELECTROLUMINESCENT DEVICE USING SAME

TECHNICAL FIELD

The present invention relates to a material for a phosphorescent light-emitting device for an organic electroluminescent device and an organic electroluminescent device using the material, and more specifically, to a thin-film-type device which emits light when an electric field is applied to a light-emitting layer formed of an organic compound.

BACKGROUND ART

In general, an organic electroluminescent device (hereinafter, referred to as organic EL device) is constructed of a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine compound and a light-emitting layer formed of an 8-hydroxyquinoline aluminum complex (hereinafter, referred to as Alq3) are provided between two electrodes as thin films, resulting in a significant improvement in luminous efficiency, compared with conventional devices in which a single crystal of anthracene molecules or the like is used. Thus, the development of the above-mentioned organic EL device has been promoted in order to accomplish its practical application to a high-performance flat panel having features such as self luminescence and rapid response.

Further, studies have been made on using phosphorescent light rather than fluorescent light as an attempt to raise the luminous efficiency of a device. Many kinds of devices including the above-mentioned device in which a hole-transporting layer formed of an aromatic diamine compound and a light-emitting layer formed of Alq3 are provided emit light by using fluorescent light emission. However, by using phosphorescent light emission, that is, by using light emission from a triplet excited state, luminous efficiency is expected to be improved by about three times to four times, compared with the case of using conventional devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet state, but highly efficient light emission has not been accomplished. In recent years, many studies centered on an organic metal complex such as an iridium complex have been made, as described in Patent Literature 1, for the purpose of attaining the high efficiency and long service life of light emission.

Citation List

Patent Literature

[PTL 1] JP 2003-515897 T
[PTL 2] JP 2001-313178 A
[PTL 3] JP 11-162650 A
[PTL 4] JP 11-176578 A

In order to obtain high luminous efficiency, host materials that are used with the dopant materials described above play an important role. Typical examples of the host materials proposed include 4,4'-bis(9-carbazolyl)biphenyl (hereinafter, referred to as CBP) as a carbazole compound disclosed in Patent Literature 2. When CBP is used as a host material for a green phosphorescent light-emitting material typified by a tris(2-phenylpyridine)iridium complex (hereinafter, referred to as Ir(ppy)3), the injection balance between charges is disturbed because CBP has the characteristic of facilitating the delivery of holes and not facilitating the delivery of electrons. Thus, excessively delivered holes flow out into an electron-transporting layer side, with the result that the luminous efficiency from Ir(ppy)3 lowers.

In order to provide high luminous efficiency to an organic EL device as described above, it is necessary to use a host material which has high triplet excitation energy and is striking a good balance in both charge (hole and electron)-injecting/transporting property. Further desired is a compound which has electrochemical stability, has high heat resistance, and has excellent amorphous stability, and hence further improvement has been demanded.

Patent Literature 3 discloses the indolocarbazole compound shown below as a hole-transporting material.

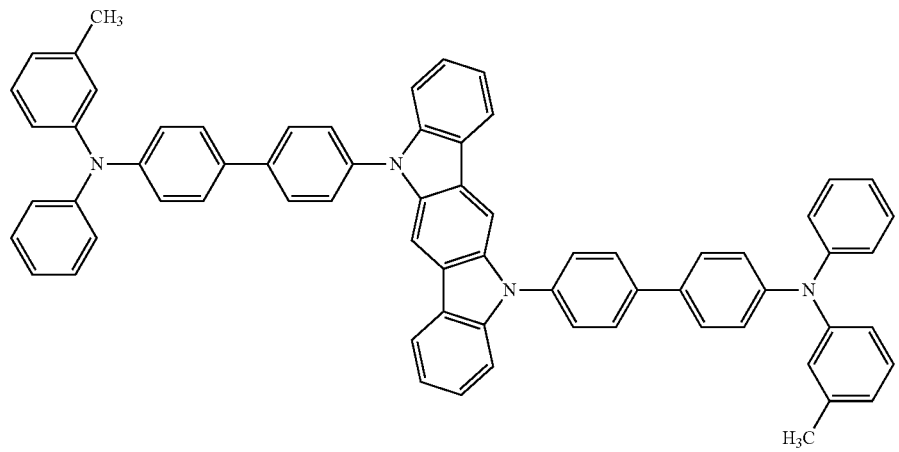 [SMILES: Cc1cccc(N(c2ccccc2)c2ccc(-c3ccc(-n4c5ccccc5c5cc6c(cc54)c4ccccc4n6-c4ccc(-c5ccc(N(c6ccccc6)c6cccc(C)c6)cc5)cc4)cc3)cc2)c1]

Moreover, Patent Literature 4 discloses the indolocarbazole compound shown below as a hole-transporting material.

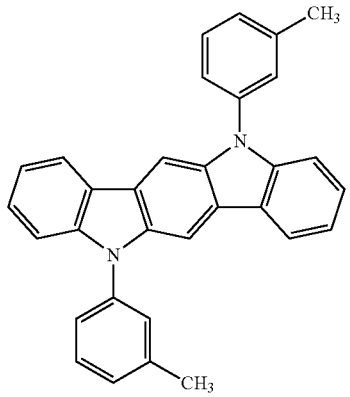 [SMILES: Cc1cccc(-n2c3ccccc3c3cc4c(cc32)c2ccccc2n4-c2cccc(C)c2)c1]

However, although the literature recommends to use these compounds having an indolocarbazole skeleton as hole-transporting materials, the literature only discloses examples of using each compound in a fluorescent light-emitting device, and does not disclose the use of the compounds as materials for a phosphorescent light-emitting device.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device which has high luminous efficiency, has high driving stability, and is practically useful and a compound suitable for the organic EL device.

The inventors of the present invention have made intensive studies and have consequently found that, when a compound having an indolocarbazole skeleton with a specific structure is used in an organic EL device, the organic EL device exhibits excellent characteristics. As a result, the present invention has been completed.

The present invention relates to a material for a phosphorescent light-emitting device, including an indolocarbazole compound represented by the following general formula (1):

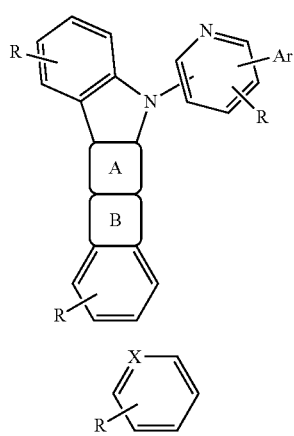

(1)

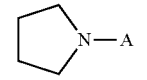

(1b)

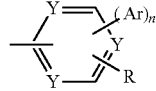

(1c)

in the general formula (1): a ring A represents an aromatic ring represented by the formula (1a) to be fused with an adjacent ring; and a ring B represents a heterocycle represented by the formula (1b) to be fused with an adjacent ring;

in the formula (1a), X represents a methine group or a nitrogen atom; in the formula (1b), A represents an aromatic hydrocarbon group having 6 to 38 carbon atoms, an alkyl group having 1 to 10 carbon atoms, a cycloalkyl group having 3 to 11 carbon atoms, or a group represented by the formula (1c); in the formula (1c): Y's each represent a methine group or a nitrogen atom, provided that at least one thereof represents a nitrogen atom; and n represent 0 or 1; in the general formulae (1) and (1c), Ar's each independently represent an aromatic hydrocarbon group having 6 to 30 carbon atoms or an aromatic heterocyclic group having 3 to 30 carbon atoms; and in the formulae (1), (1a), and (1c), R's each independently represent a hydrogen atom, an alkyl group having 1 to 10 carbon atoms, or a cycloalkyl group having 3 to 11 carbon atoms.

Of the indolocarbazole compounds each represented by the general formula (1), an indolocarbazole derivative represented by the following general formula (2) is given as a preferred compound:

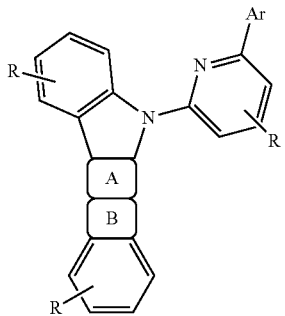

(2)

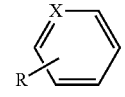

(1a)

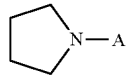

(1b)

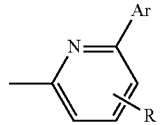

(2c)

in the formulae, a ring A, a ring B, Ar's, X, n, and R's have the same meanings as those in the general formula (1); and in the formula (1b), A represents an aromatic hydrocarbon group having 6 to 38 carbon atoms or an aromatic heterocyclic group represented by the formula (2c).

Of the indolocarbazole compounds each represented by the general formula (2), an indolocarbazole compound in which A represents an aromatic hydrocarbon group having 6 to 38 carbon atoms except a fused ring structure or an aromatic heterocyclic group represented by the formula (2c) is given as a preferred compound. Further, an indolocarbazole compound in which Ar represents an aromatic hydrocarbon group except a fused ring structure or an aromatic heterocyclic group is given as a more preferred compound.

Of the indolocarbazole compounds each represented by the general formula (1) or (2), indolocarbazole compounds represented by the following general formulae (3) to (6) are given as more preferred compounds.

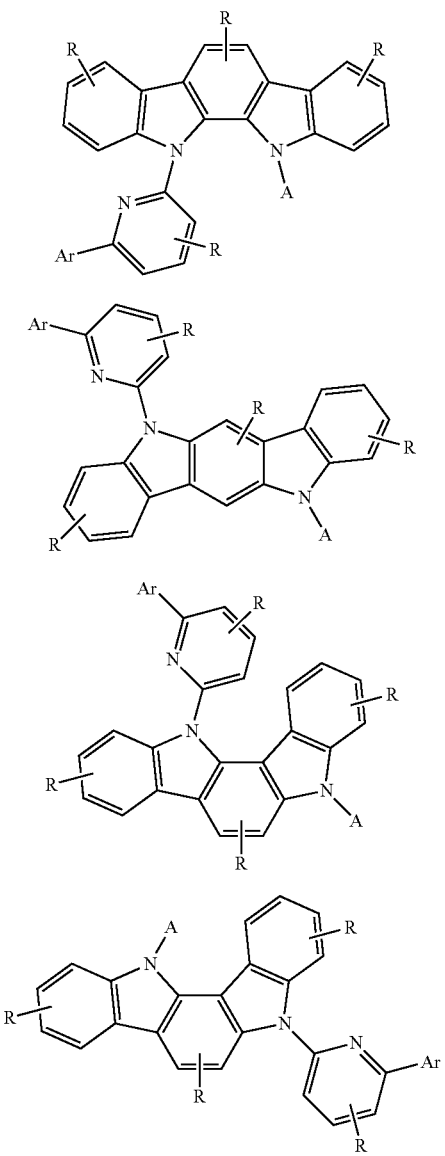

In the general formulae (3) to (6), A's, Ar's, and R's have the same meanings as those in the general formula (1) or (2).

The present invention also relates to an organic electroluminescent device, including an anode, an organic layer, and a cathode laminated on a substrate, in which the organic electroluminescent device includes an organic layer containing the above-mentioned material for a phosphorescent light-emitting device.

DESCRIPTION OF EMBODIMENTS

Figure 1:
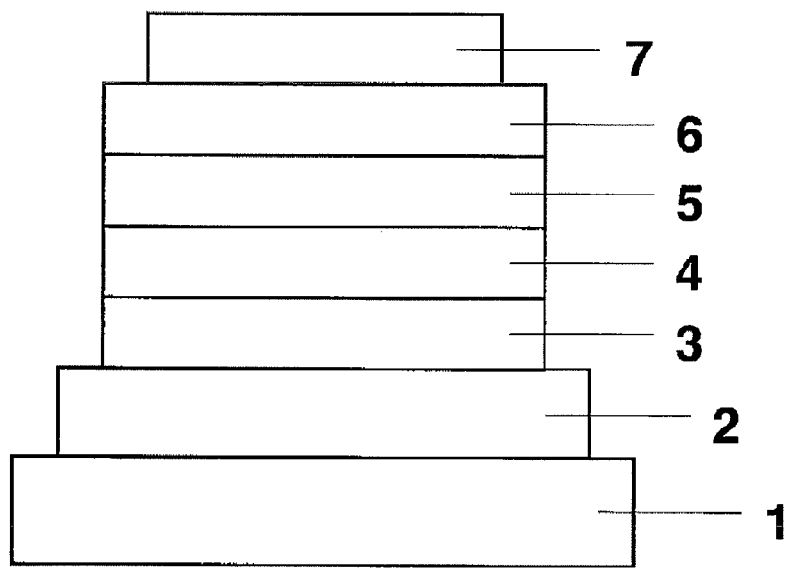
FIG. 1 is a cross-sectional view showing one structural example of an organic EL device.

A material for a phosphorescent light-emitting device of the present invention is an indolocarbazole compound represented by the general formula (1). It is conceivable the material for a phosphorescent light-emitting device has a structure in which one nitrogen atom of the indolocarbazole compound is substituted with pyridine and pyridine is substituted with one aromatic hydrocarbon or aromatic heterocyclic group and thus exerts an excellent effect.

In the general formula (1), a ring A is represented by the formula (1a) to be fused with an adjacent ring, and a ring B is a heterocycle represented by the formula (1b) to be fused with an adjacent ring.

The general formula (1) or (2) encompasses the formulae (1a), (1b), and (1c) or the formula (2c). Hence, by the general formula (1) or (2) as used herein is meant to include those formulae in some cases. Further, descriptions about the general formula (1) are common to descriptions about the general formula (2) in many parts. It should be therefore understood that the common parts also serve as the descriptions about the general formula (2).

In the indolocarbazole compound represented by the general formula (1), an aromatic ring represented by the formula (1a) may be fused with two adjacent rings at any position, but there is a position at which the aromatic ring cannot be fused with the rings from the structural viewpoint. The aromatic ring represented by the formula (1a) has six sides, and is not fused with the two adjacent rings through two adjacent sides. Further, the heterocycle represented by the formula (1b) may be fused with two adjacent rings at any position, but there is a position at which the heterocycle cannot be fused with the rings from the structural viewpoint. That is, the heterocycle represented by the formula (1b) has five sides, and is not fused with the two adjacent rings through two adjacent sides and is not fused with an adjacent ring through a side including a nitrogen atom. Thus, there is a limitation on the kind of an indolocarbazole skeleton.

In the general formula (1), the indolocarbazole skeleton is preferably represented by any one of the following forms. Preferred fusion positions of an aromatic hydrocarbon ring and a heterocycle in the indolocarbazole skeleton are understood from these examples.

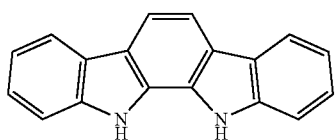

(IC-1)

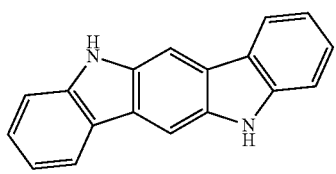

(IC-2)

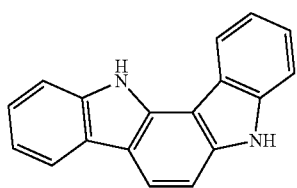

(IC-3)

In the general formula (1), in the formula (1a), X represents a methine group or a nitrogen atom, preferably a methine group.

In the general formula (1), in the formula (1b), A represents an aromatic hydrocarbon group having 6 to 38 carbon atoms, an alkyl group having 1 to 10 carbon atoms, a cycloalkyl group having 3 to 11 carbon atoms, or a group represented by the formula (1c), preferably an aromatic hydrocarbon group having 6 to 18 carbon atoms, an alkyl group having 1 to 8 carbon atoms, a cycloalkyl group having 3 to 8 carbon atoms, or a group represented by the formula (1c).

Specific examples of the aromatic hydrocarbon group include a monovalent group produced by removing a hydrogen atom from benzene, naphthalene, fluorene, phenalene, anthracene, phenanthrene, fluoranthene, pyrene, chrysene, tetraphene, tetracene, naphthacene, rubrene, picene, perylene, pentaphene, or an aromatic compound in which a plurality of aromatic rings are linked together. Of those, a monovalent group produced by removing a hydrogen atom from naphthalene, fluorene, phenalene, anthracene, phenanthrene, fluoranthene, or an aromatic compound in which a plurality of aromatic rings are linked together is preferably given. When an aromatic hydrocarbon group in which a plurality of aromatic rings are linked together is employed, the aromatic hydrocarbon group may be formed by linking a plurality of aromatic rings together with pyridine, pyrimidine, triazine, quinoline, isoquinoline, carbazole, or the like. The above-mentioned aromatic hydrocarbon group may have a substituent. When the aromatic hydrocarbon group has a substituent, the substituent is preferably an alkyl group having 1 to 4 carbon atoms, a cycloalkyl group having 3 to 6 carbon atoms, an alkoxy group having 1 or 2 carbon atoms, an acetyl group, or a diarylamino group having 6 to 12 carbon atoms.

Here, the monovalent group produced by the linkage of a plurality of aromatic rings is, for example, represented by any one of the following formulae.

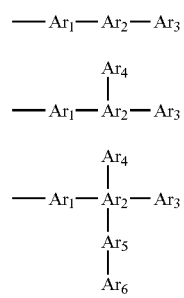

(In the formulae (11) to (13), $Ar_1$ to $Ar_6$ each represent a substituted or unsubstituted aromatic ring.)

When a plurality of aromatic rings are herein linked together, the aromatic hydrocarbon group refers to a case where $Ar_1$ in the formulae (11) to (13) represents an aromatic hydrocarbon, and the aromatic heterocyclic group refers to a case where $Ar_1$ represents an aromatic heterocycle, for example. Further, the phrase "except a fused ring structure" means a case where $Ar_1$ does not represent a fused ring structure. Further, in this case, $Ar_2$ to $Ar_6$ may be identical to or different from each other.

Specific examples of the aromatic hydrocarbon group produced by removing a hydrogen atom from an aromatic compound in which a plurality of aromatic rings are linked together described above include a monovalent group produced from, for example, biphenyl, terphenyl, phenylnaphthalene, phenylanthracene, bistriazylbenzene, phenylpyridine, diphenylpyridine, diphenylpyrimidine, diphenyltriazine, or phenylcarbazole. The position at which the group is linked to a nitrogen atom of the indolocarbazole is not particularly limited, and may be on a terminal ring or on a middle ring. However, a ring to be bonded to the nitrogen atom is preferably one except a fused ring structure. When the group produced from the aromatic compound in which a plurality of aromatic rings are linked together is employed, the number of the rings to be linked together is preferably 2 to 5, more preferably 2 or 3. The above-mentioned aromatic hydrocarbon group or aromatic heterocyclic group may have a substituent. When the aromatic hydrocarbon group or aromatic heterocyclic group has a substituent, the substituent is preferably an alkyl group having 1 to 4 carbon atoms, a cycloalkyl group having 3 to 6 carbon atoms, an alkoxy group having 1 or 2 carbon atoms, an acetyl group, or a diarylamino group having 6 to 12 carbon atoms.

The number of carbon atoms in the group having a substituent to be calculated in this description includes the number of carbon atoms in the substituent.

In the formula (1b), preferred specific examples of A representing an alkyl group having 1 to 10 carbon atoms or a cycloalkyl group having 3 to 11 carbon atoms include a monovalant group produced by removing a hydrogen atom from methane, ethane, t-butane, n-octane, or cyclohexane. The above-mentioned alkyl group or cycloalkyl group may have a substituent. When the alkyl group or cycloalkyl group has a substituent, the substituent is preferably an alkoxy group having 1 or 2 carbon atoms, an acetyl group, an aryl group having 6 to 12 carbon atoms, or a heteroaryl group having 3 to 12 carbon atoms, more preferably a phenyl group, a naphthyl group, a carbazolyl group, a quinolyl group, or an isoquinolyl group.

In the formula (1b), a preferred form of A is, for example, an aromatic hydrocarbon group having 6 to 38 carbon atoms or a group represented by the formula (1c), and a more preferred form thereof is, for example, an aromatic hydrocarbon group having 6 to 38 carbon atoms except a fused ring structure or a group represented by the formula (1c).

In the formula (1c), Y's each represent a methine group or a nitrogen atom, and at least one thereof represents a nitrogen atom. It is preferred that one of Y's represent a nitrogen atom.

In the formula (1c), n represents 0 or 1 and n preferably represents 1.

As a preferred form, there is given an aromatic heterocyclic group represented by the formula (2c) having a limited structure of the formula (1c).

In the general formula (1), Ar represents an aromatic hydrocarbon group having 6 to 30 carbon atoms or an aromatic heterocyclic group having 3 to 30 carbon atoms. Ar preferably represents a monovalent aromatic hydrocarbon group having 6 to 18 carbon atoms or an aromatic heterocyclic group having 3 to 17 carbon atoms. Preferred specific examples of Ar include a monovalent group produced by removing a hydrogen atom from benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, phenanthridine, phenanthroline, acridine, phenazine, phenoxazine, phenothiazine, anthyridine, or an aromatic compound in which a plurality of those aromatic rings are linked together. Ar preferably represents a group in which a fused ring structure is not formed, and specific examples thereof include a monovalent group produced by removing a hydrogen atom from benzene, pyridine, pyrimidine, triazine, or an aromatic compound in which a plurality of those aromatic rings are linked together. When a plurality of the above-mentioned aromatic rings are linked together, the rings may be identical to or different from each other.

Specific examples of the group produced by removing a hydrogen atom from an aromatic compound in which a plurality of the above-mentioned aromatic rings are linked together include a monovalent group produced from, for example, biphenyl, terphenyl, bipyridine, bipyrimidine, bitriazine, bistriazylbenzene, phenylpyridine, diphenylpyridine, diphenylpyrimidine, diphenyltriazine, phenylcarbazole, or pyridylcarbazole. The position at which the group is linked to a pyridine ring is not particularly limited, and may be on a terminal ring or on a middle ring. However, a ring to be bonded to the pyridine ring is preferably one except a fused ring structure. When the group produced from the aromatic compound in which a plurality of aromatic rings are linked together is employed, the number of the aromatic rings to be linked together is preferably 2 to 5, more preferably 2 or 3. The above-mentioned aromatic hydrocarbon group and aromatic heterocyclic group may have a substituent. When any one of the aromatic hydrocarbon group and aromatic heterocyclic group has a substituent, the substituent is preferably an alkyl group having 1 to 4 carbon atoms, an alkoxy group having 1 or 2 carbon atoms, or an acetyl group.

In the general formula (1), R's each independently represent a hydrogen atom, an alkyl group having 1 to 10 carbon atoms, or a cycloalkyl group having 3 to 11 carbon atoms, preferably a hydrogen atom, an alkyl group having 1 to 4 carbon atoms, or a cycloalkyl group having 3 to 6 carbon atoms, more preferably a hydrogen atom.

Of the indolocarbazole compounds each represented by the general formula (1), an indolocarbazole compound represented by the above-mentioned general formula (2) is given as a preferred compound, and indolocarbazole compounds represented by the general formulae (3) to (6) are given as more preferred compounds.

In the general formulae (1) to (6), it is interpreted that the same symbols and formulae have the same meanings unless otherwise particularly specified. For example, A in the general formula (1) and A in the general formula (2) differ from each other in definition of a group included therein. It is therefore understood that those are particularly specified.

The indolocarbazole compounds represented by the general formulae (1) to (6) may each be synthesized by selecting materials depending on the structure of the target compound and using a known technique.

For example, an indolocarbazole skeleton of the indolocarbazole compound represented by the general formula (3) maybe synthesized in accordance with the following reaction formula with reference to a synthesis example disclosed in Synlett, 2005, No. 1, p 42-48.

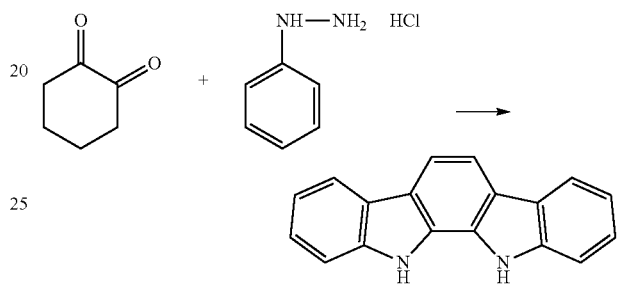

Further, an indolocarbazole skeleton represented by the general formula (4) may be synthesized in accordance with the following reaction formula with reference to a synthesis example disclosed in Archiv der Pharmazie (Weinheim, Germany), 1987, 320(3), p 280-2.

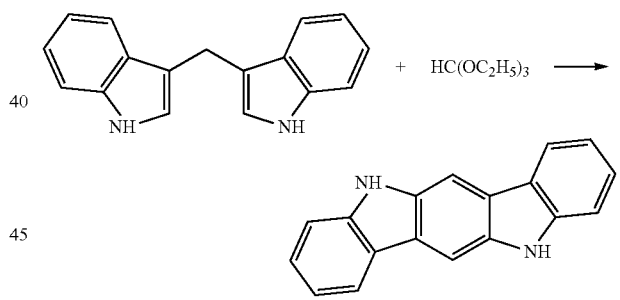

In addition, indolocarbazole skeletons represented by the general formulae (5) and (6) may be synthesized in accordance with the following reaction formulae with reference to synthesis examples disclosed in The Journal of Organic Chemistry, 2007, 72(15)5886 and Tetrahedron, 1995, 55, p 2371.

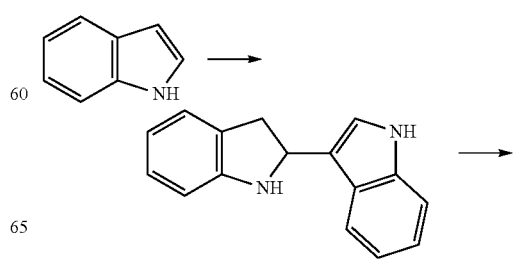

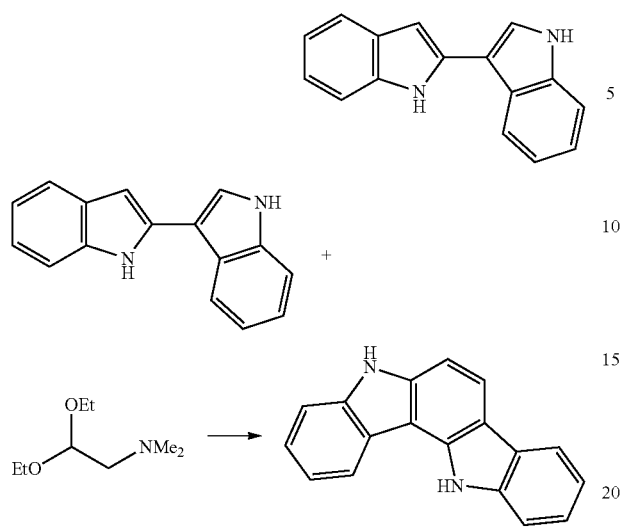

A group of compounds of the present invention represented by the general formulae (1) to (6) may be synthesized by substituting a hydrogen atom on a nitrogen atom in each of the indolocarbazole skeletons obtained in accordance with the above-mentioned reaction formulae by the corresponding aromatic group in accordance with a conventional method.

Specific examples of the indolocarbazole compound represented by the general formula (1) are shown below, but the material for a phosphorescent light-emitting device of the present invention is not limited to these examples.

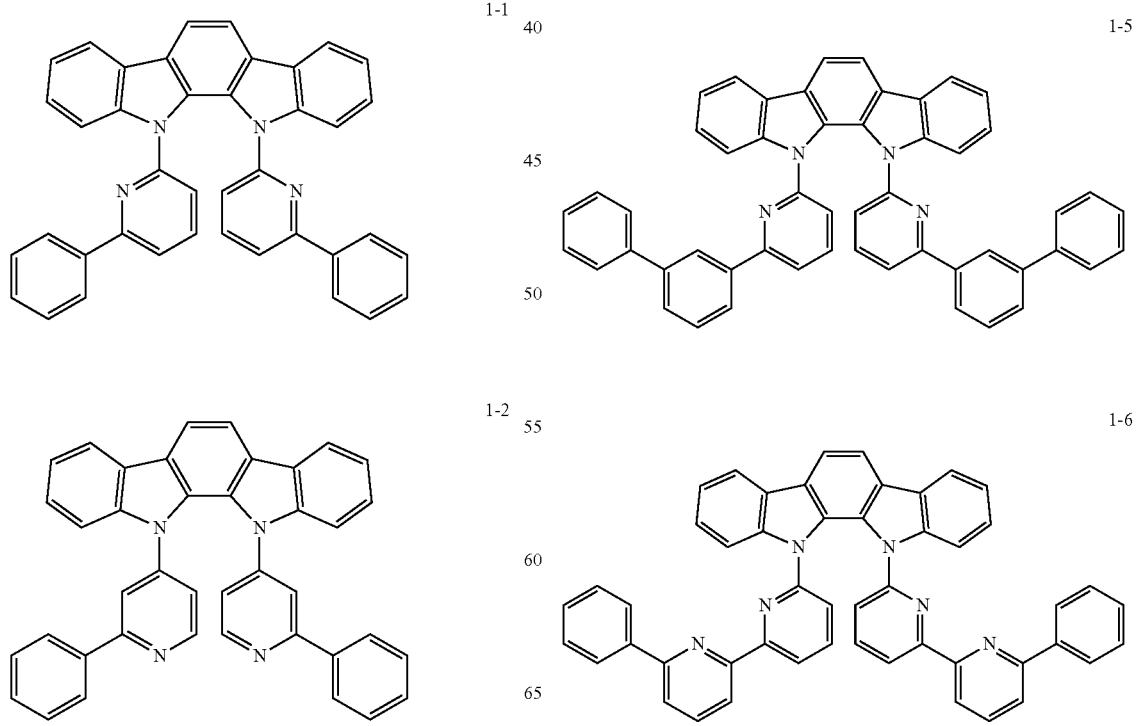

1-7
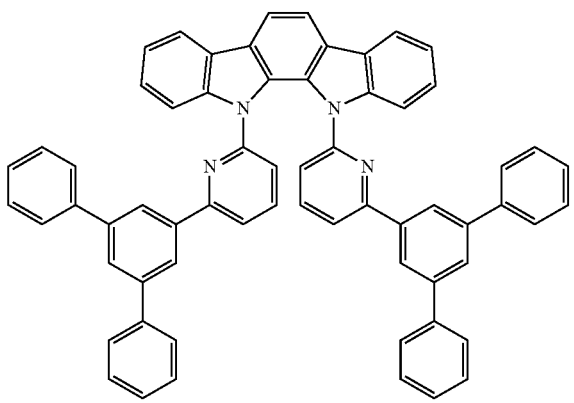
1-8
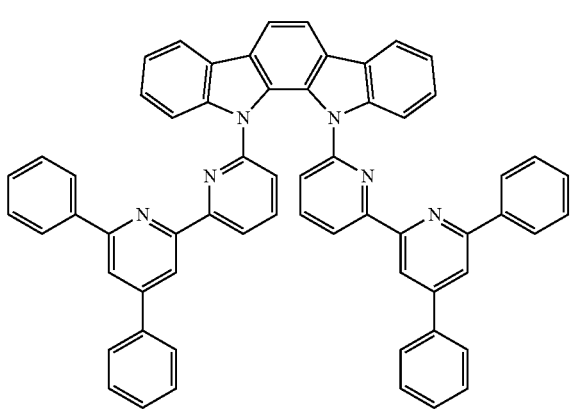
1-9
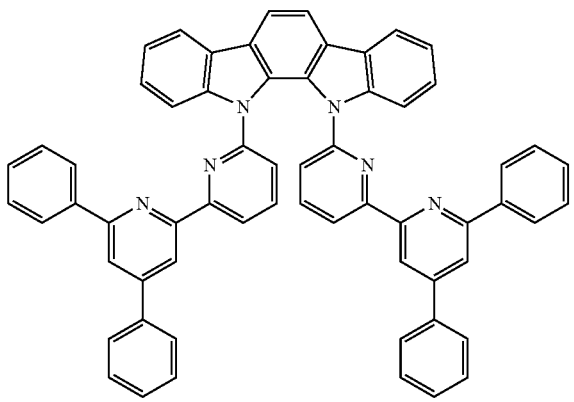
1-10
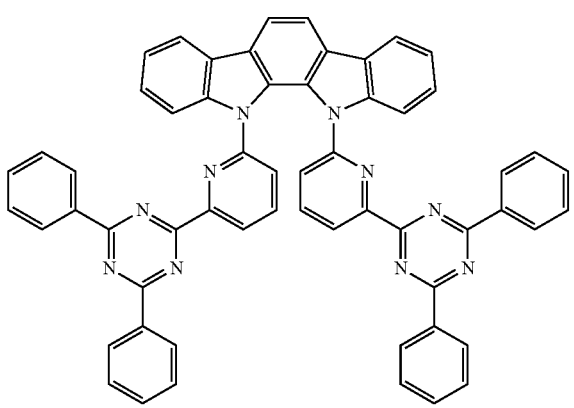
1-11
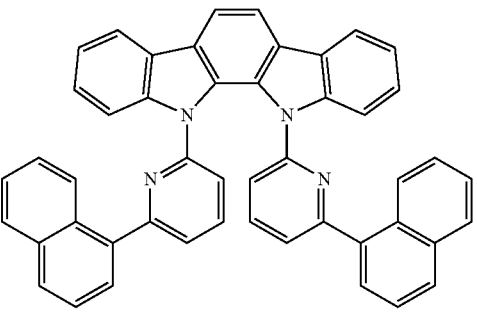
1-12
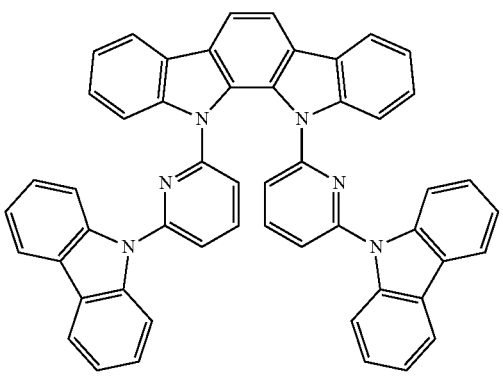
1-13
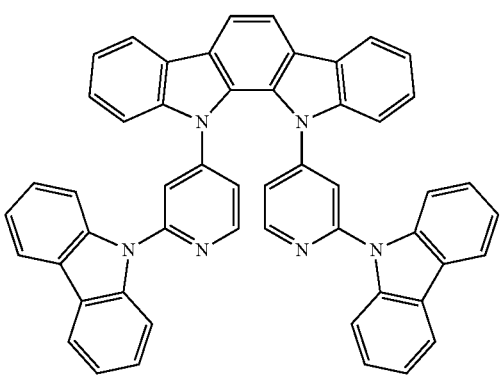
1-14
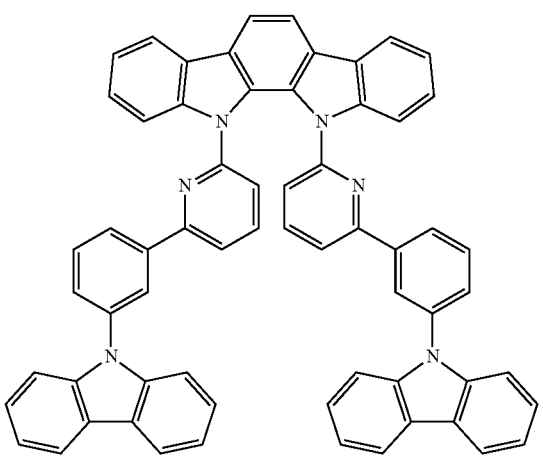

1-15
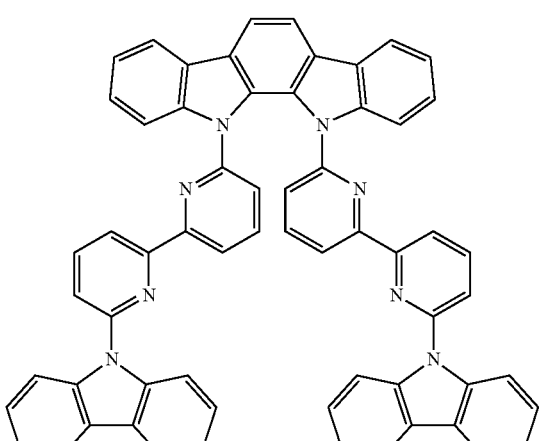
1-16
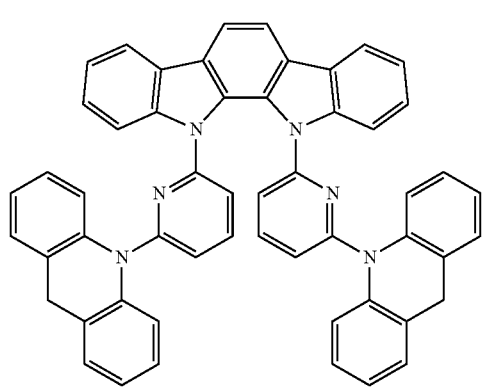
1-17
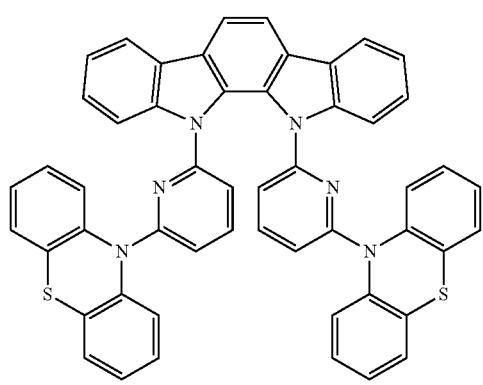
1-18
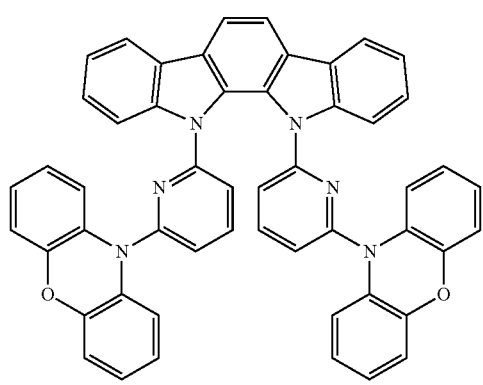
1-19
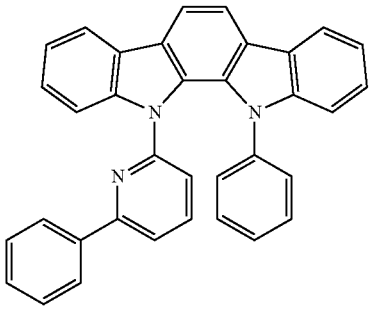
1-20
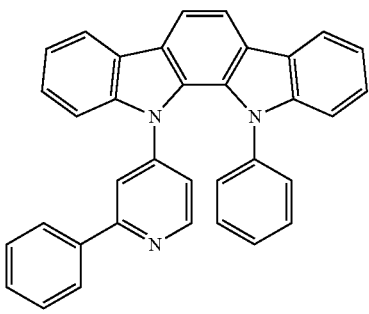
1-21
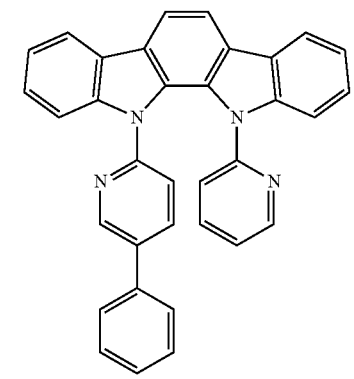
1-22
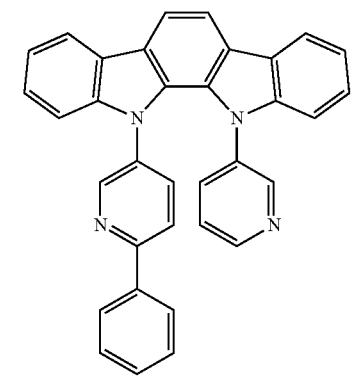

-continued
1-23
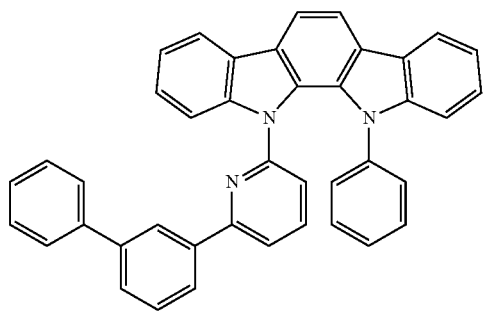
1-24
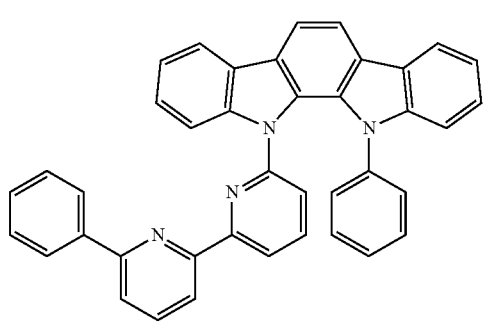
1-25
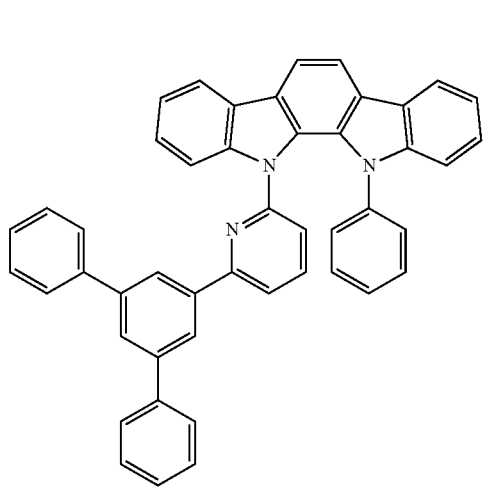
1-26
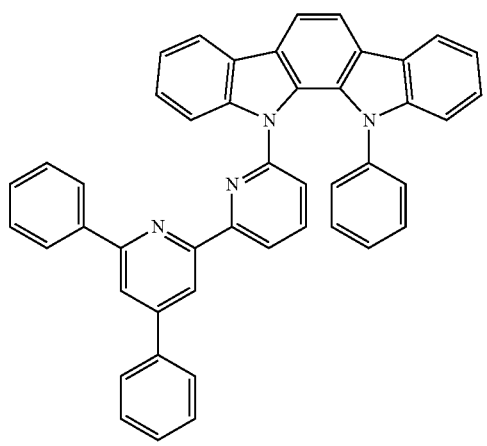
-continued
1-27
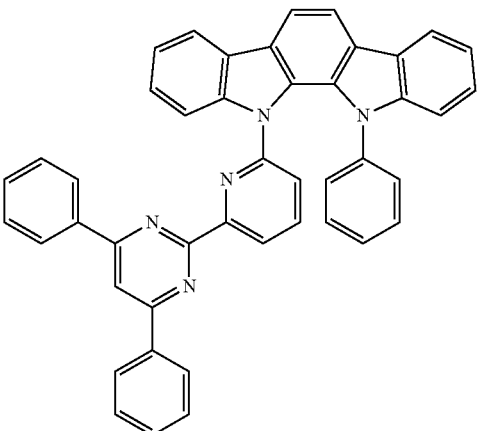
1-28
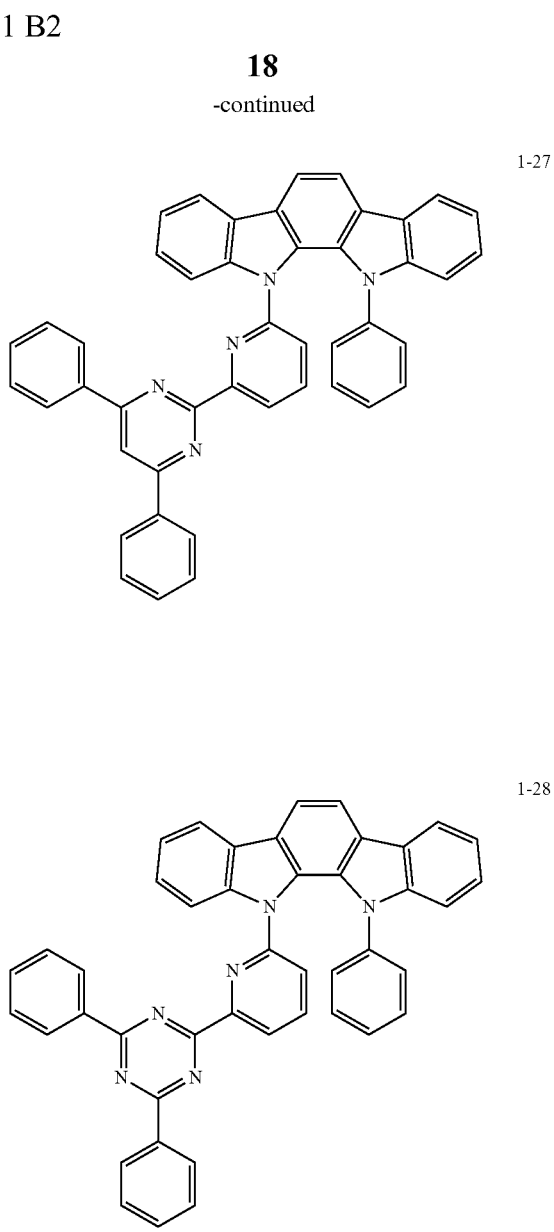
1-29
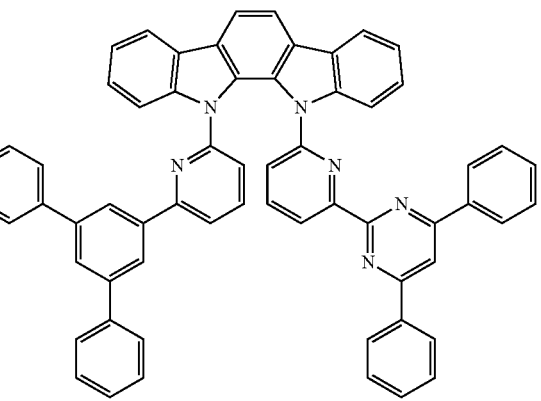

1-30
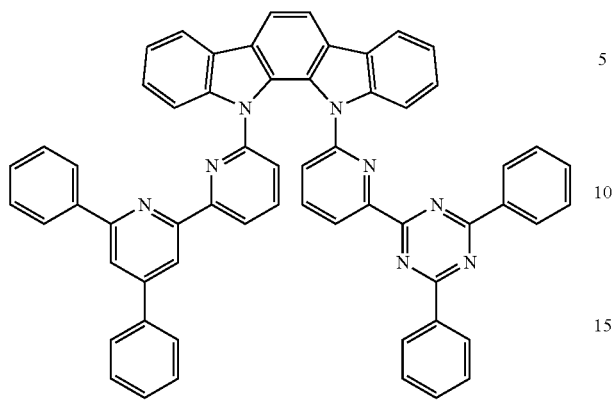
1-31
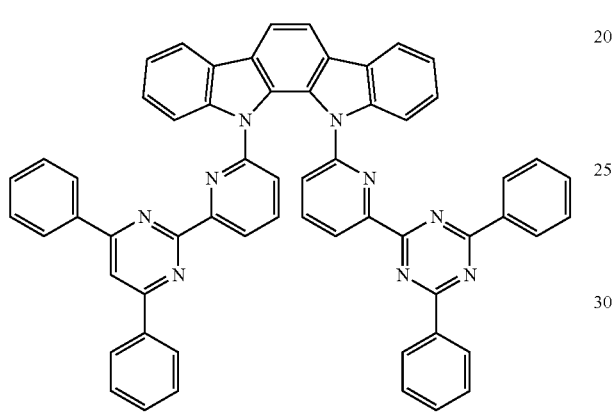
1-32
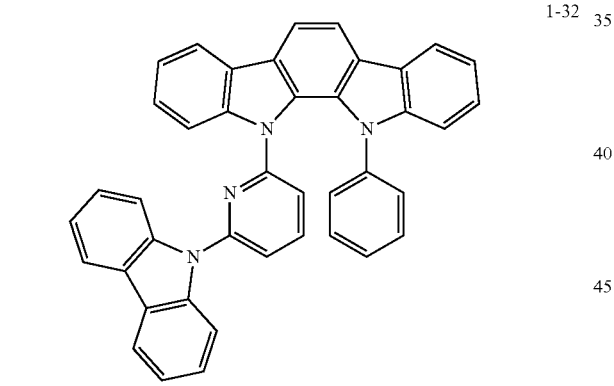
1-33
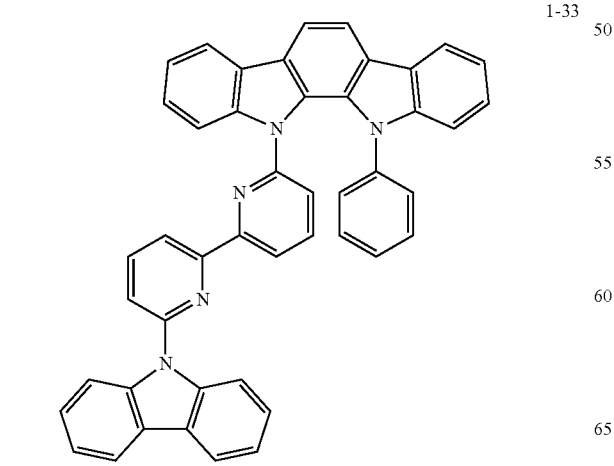
1-34
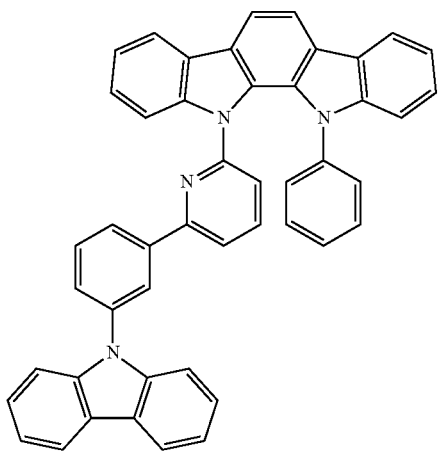
1-35
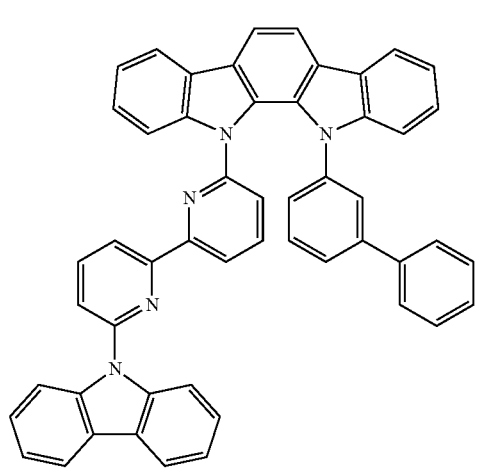
1-36
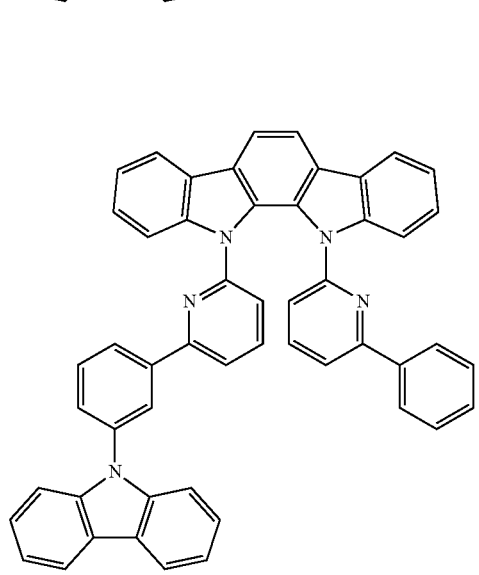

1-37
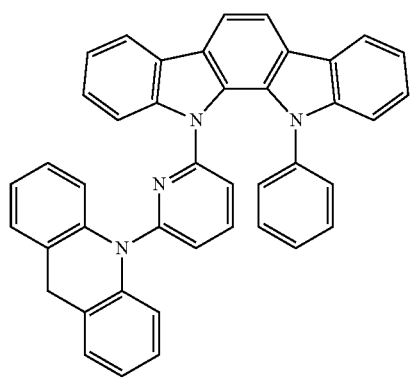
1-38
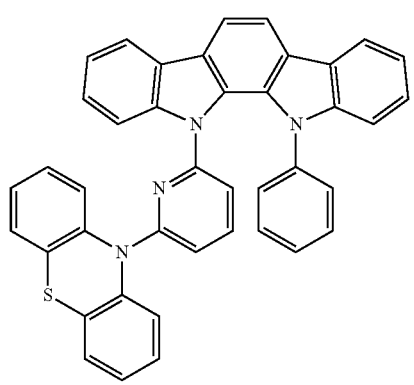
1-39
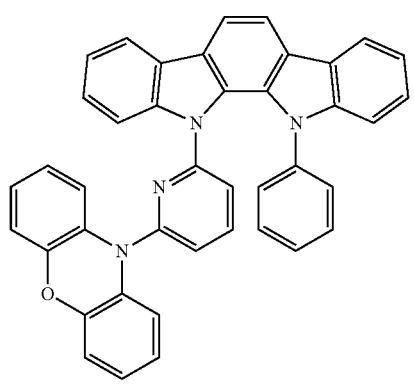
1-40
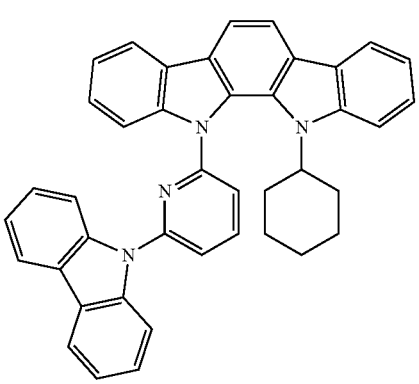
1-41
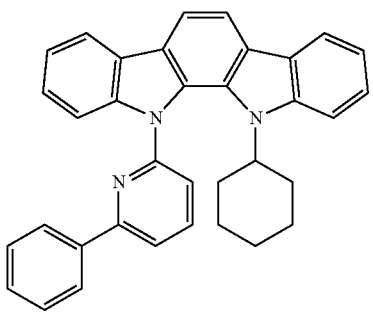
1-42
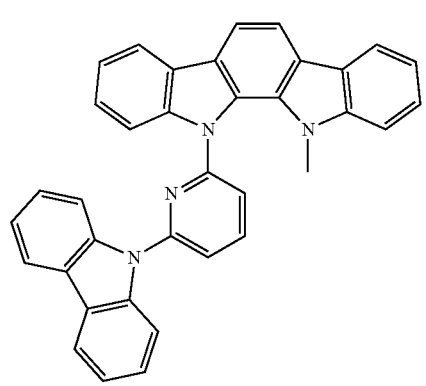
1-43
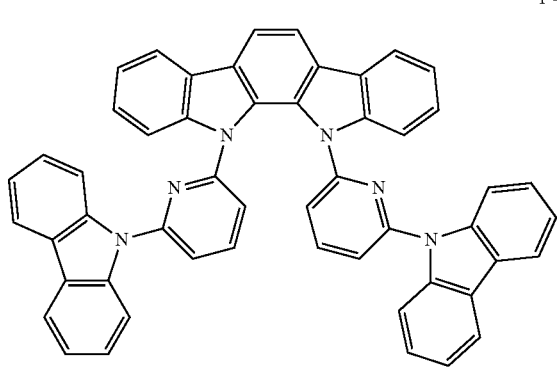
1-44
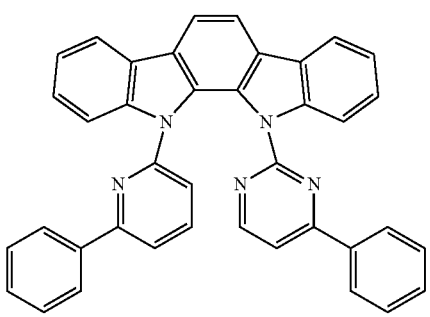

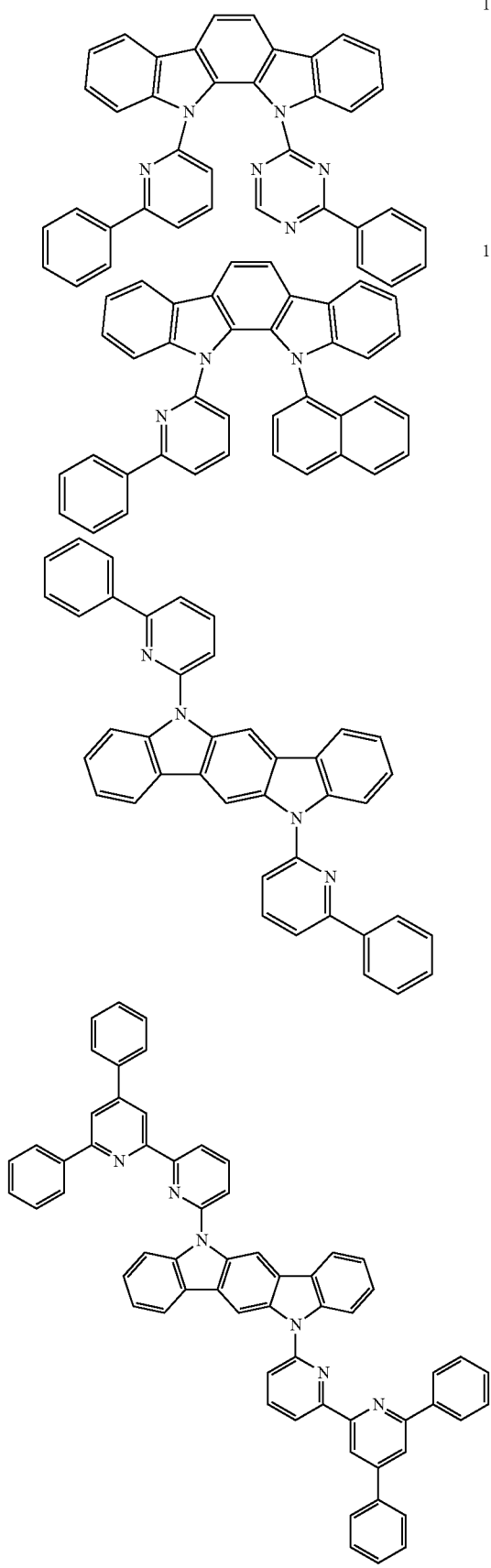
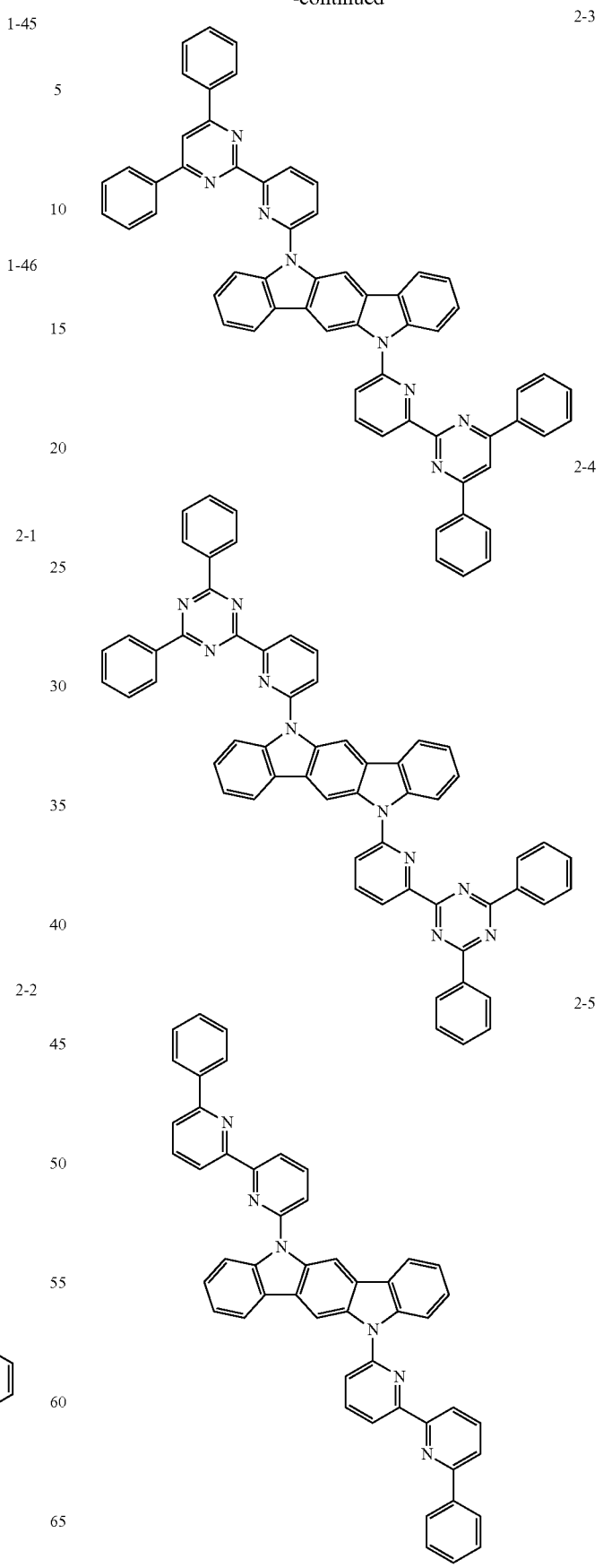

2-6
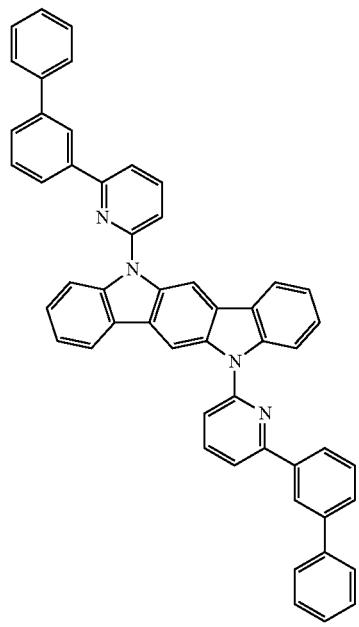
2-7
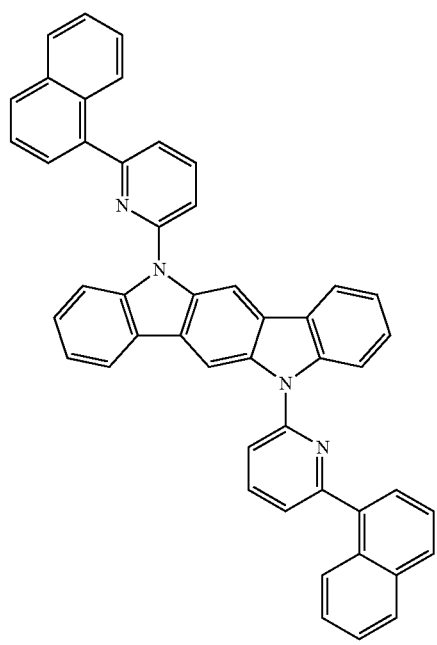
2-8
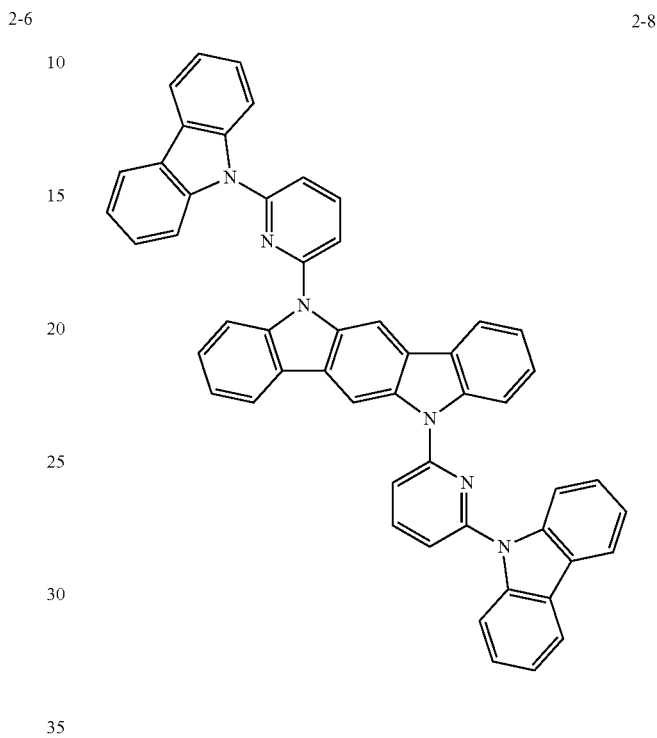
2-9
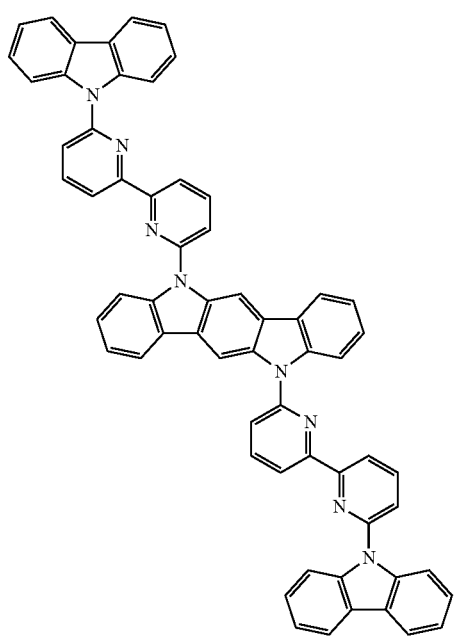

2-10
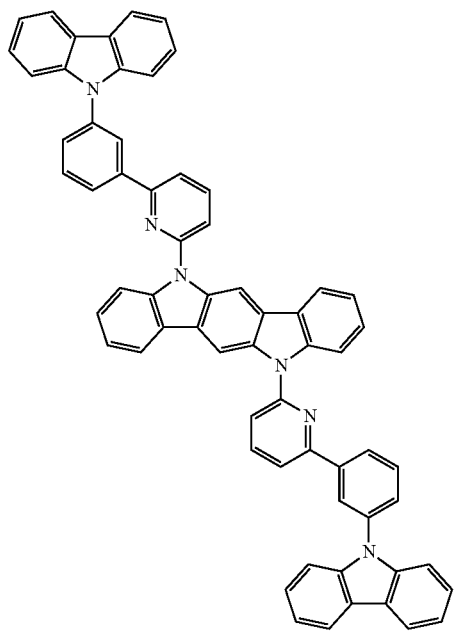
2-11
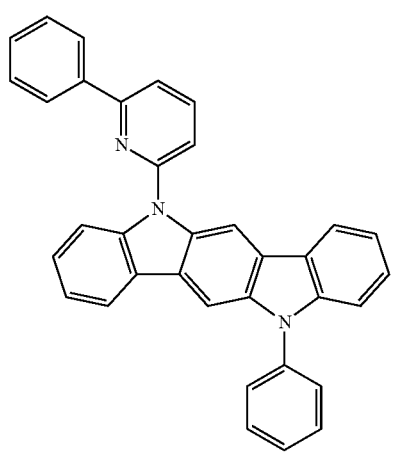
2-13
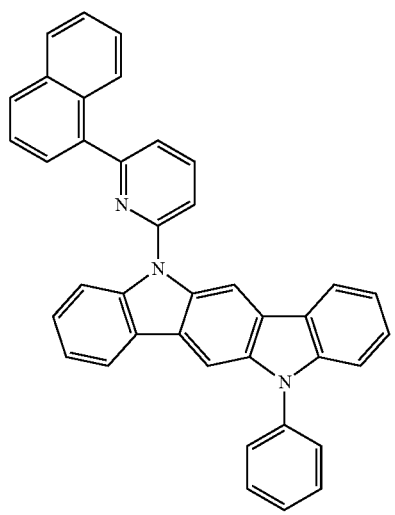
2-14
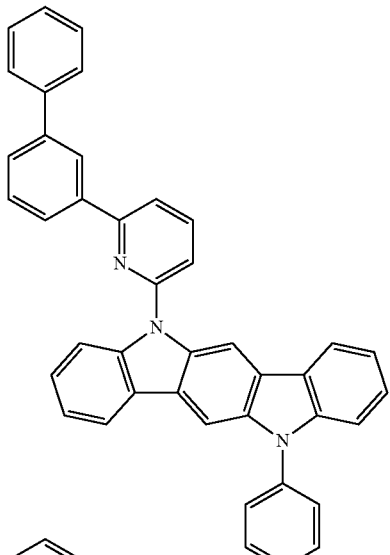
2-15
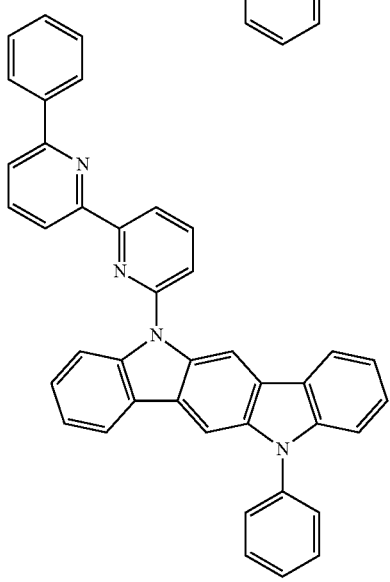
2-16
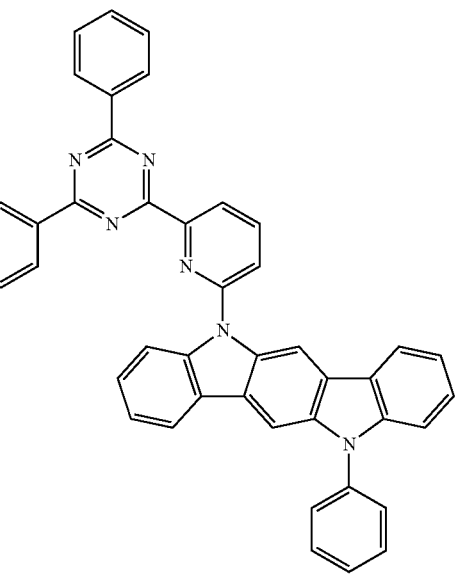

-continued
2-17
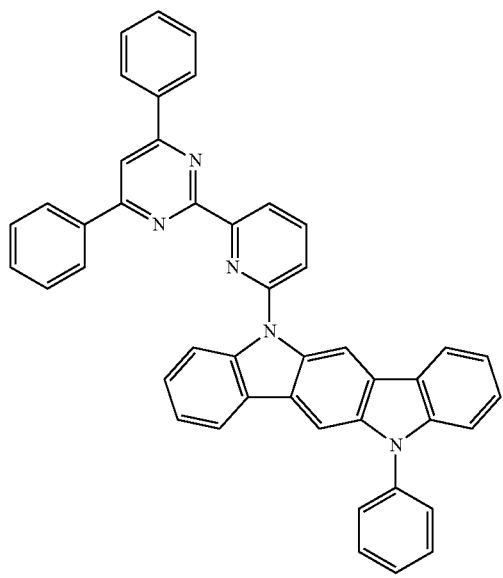
2-18
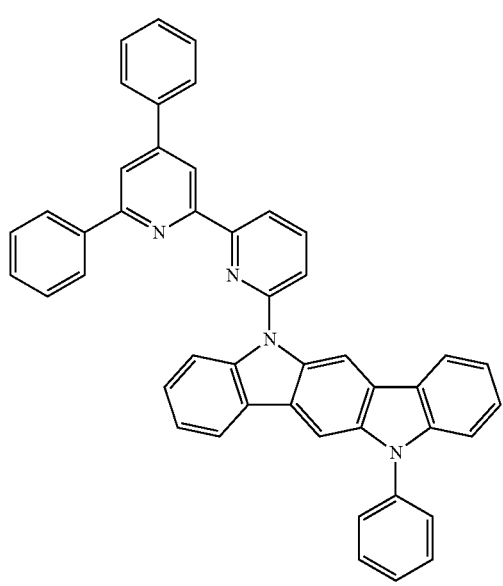
2-19
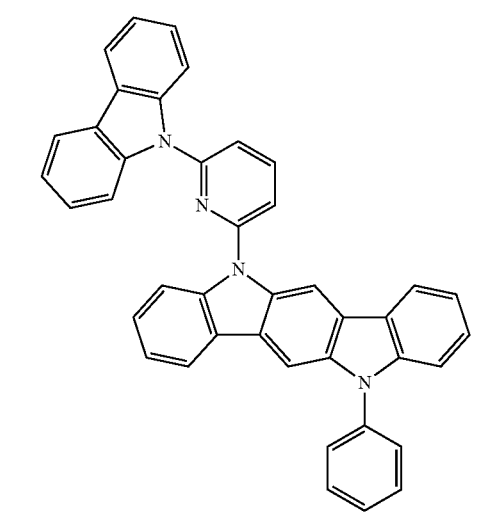
-continued
2-20
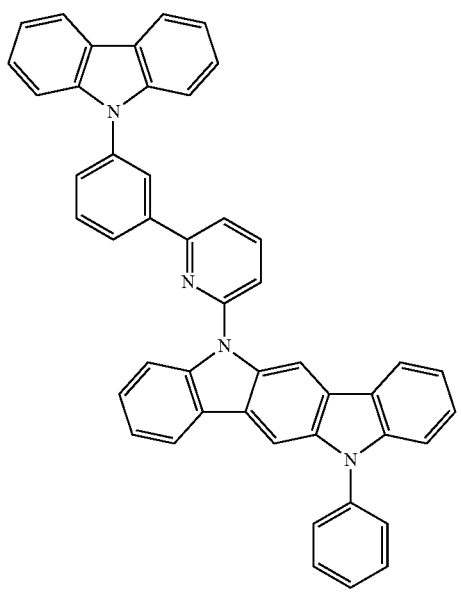
2-21
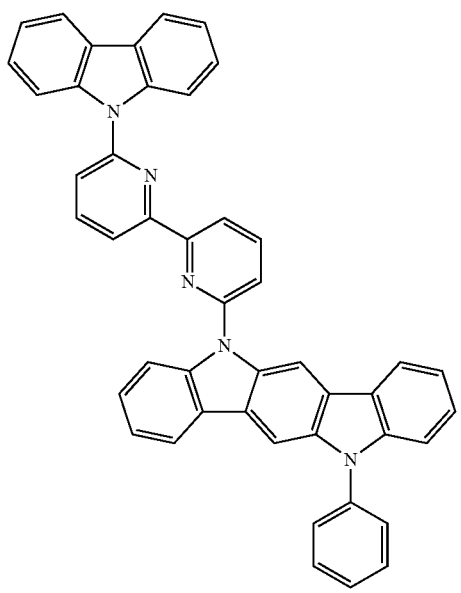
3-1
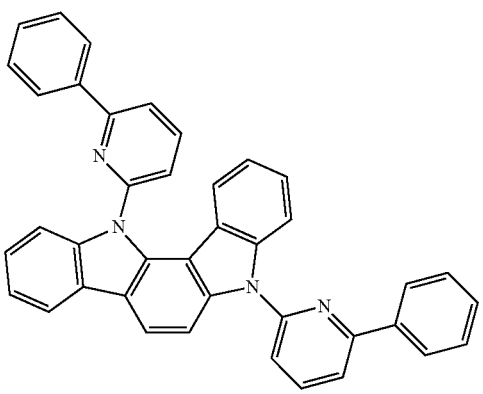

3-2
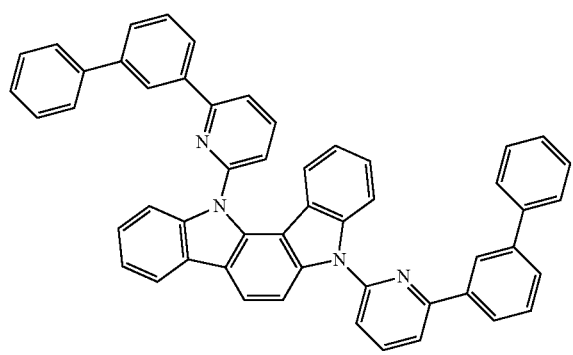
3-3
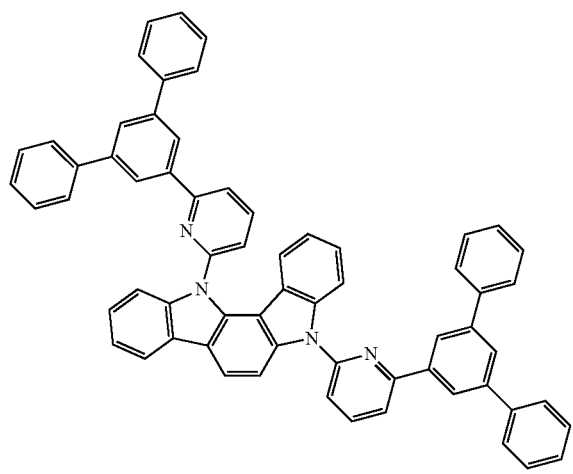
3-4
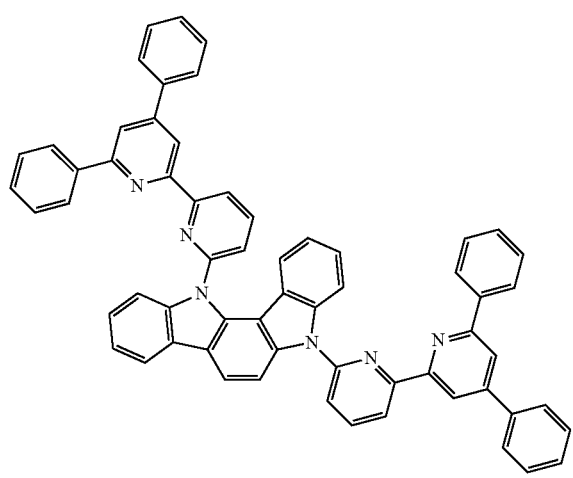
3-5
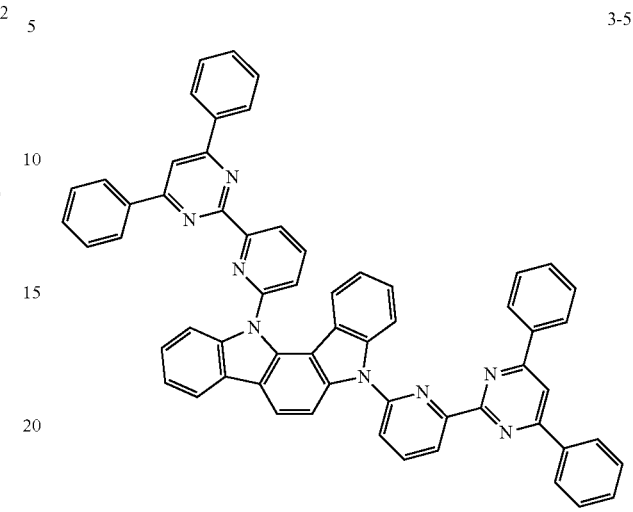
3-6
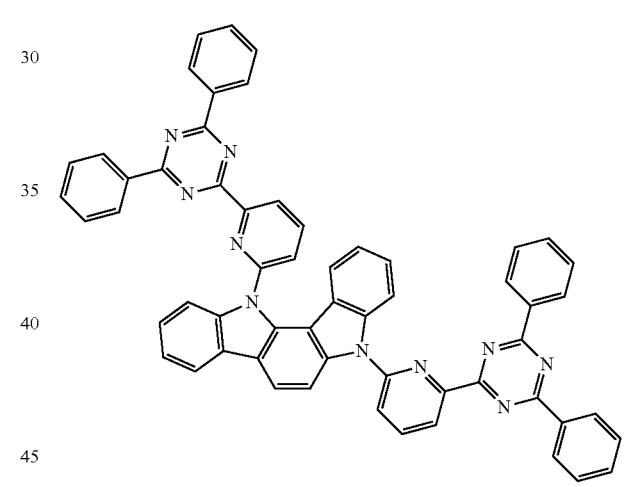
3-7
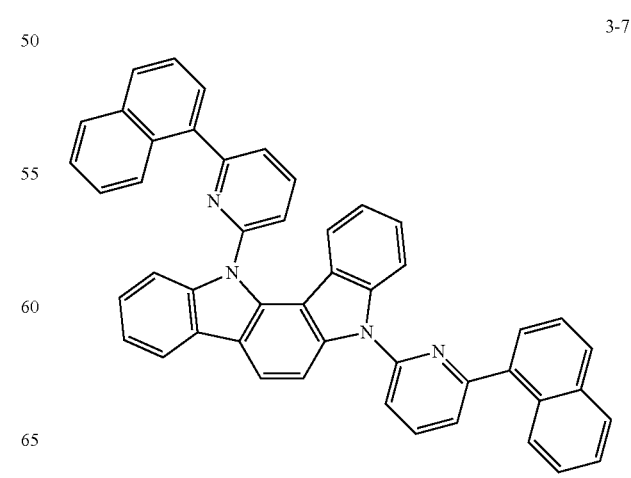

3-8
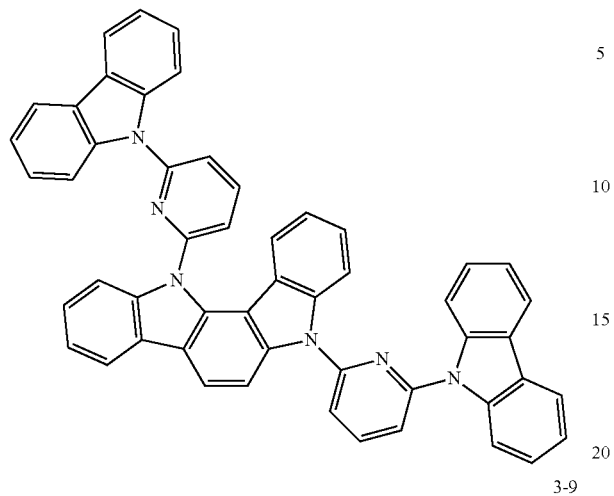
3-9
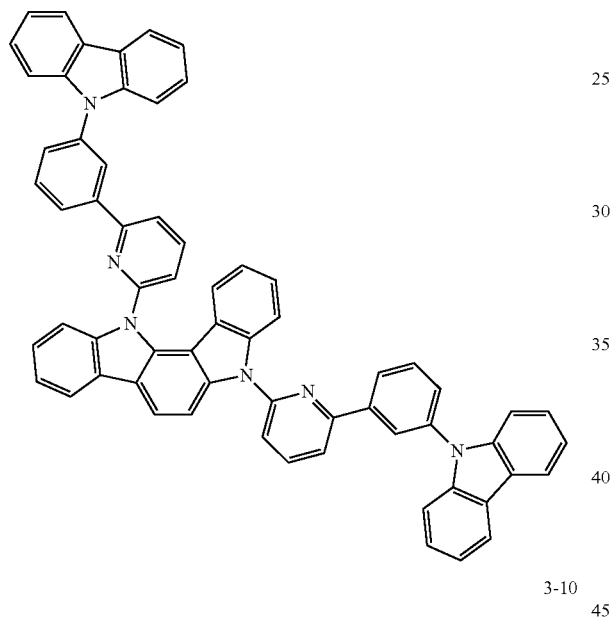
3-10
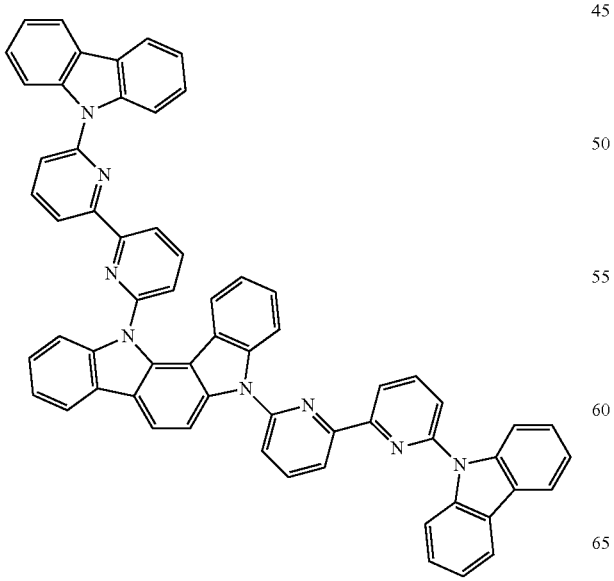
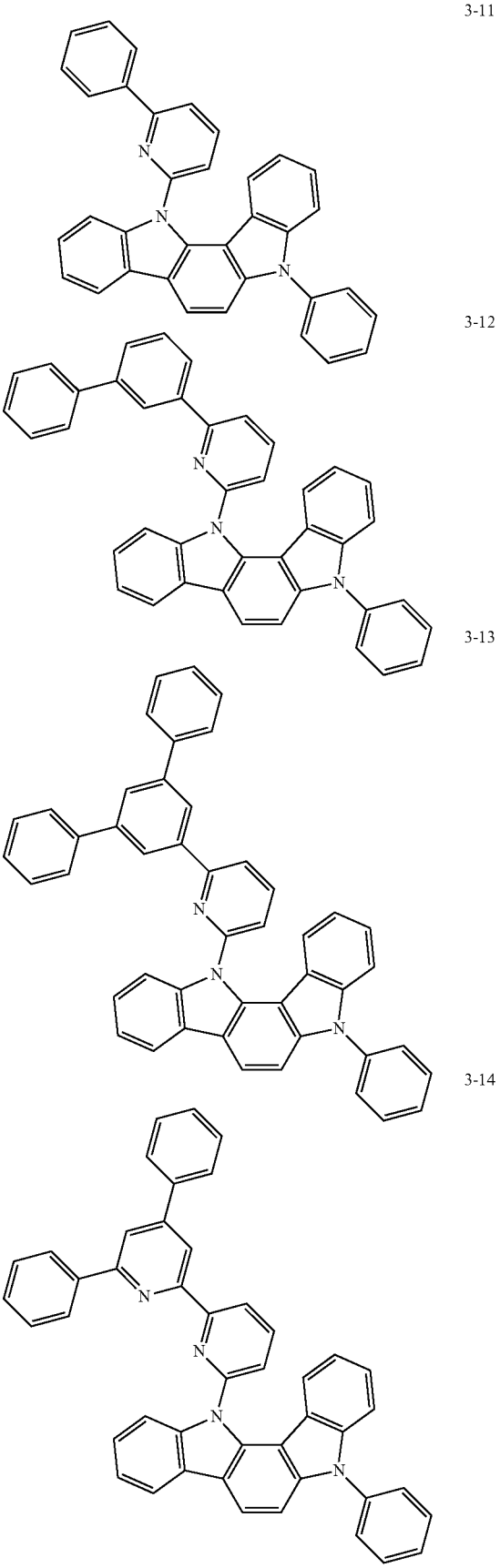
3-11
3-12
3-13
3-14

3-15
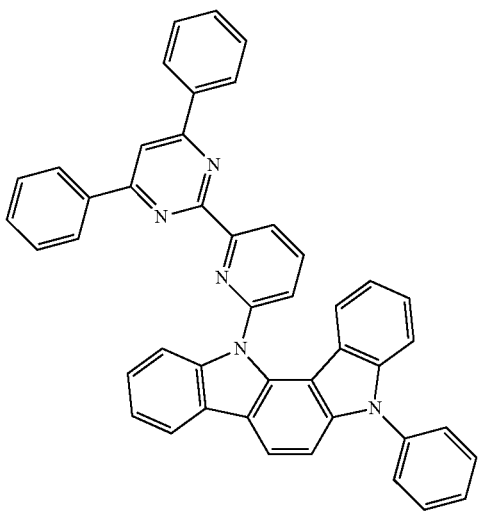
3-16
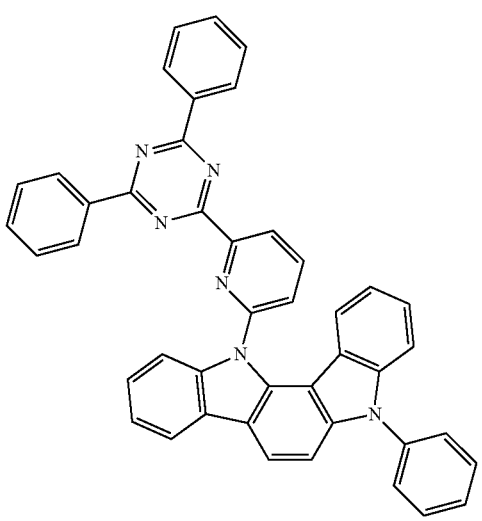
3-17
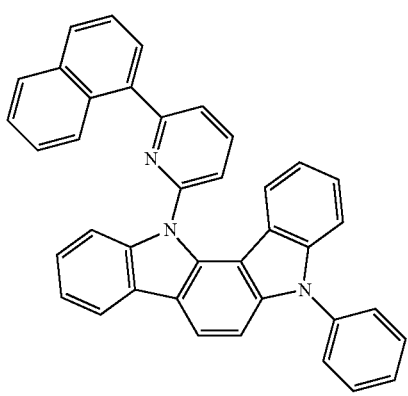
3-18
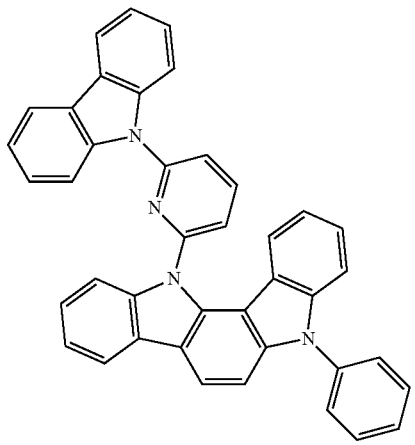
3-19
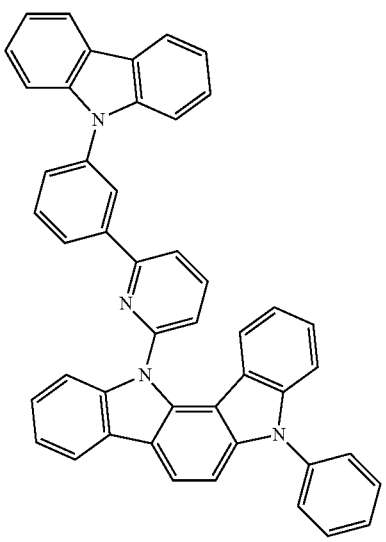
3-20
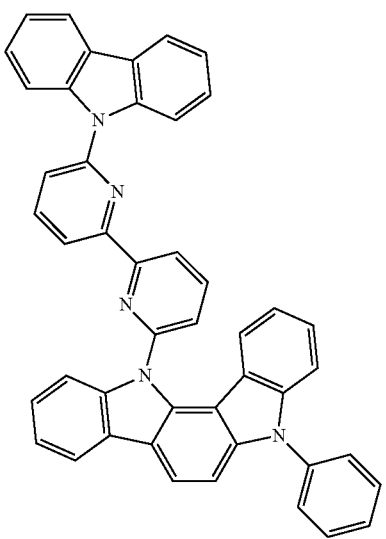

3-21
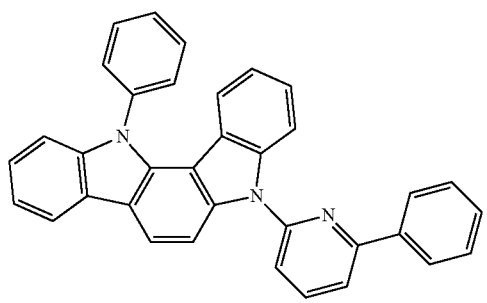
3-25
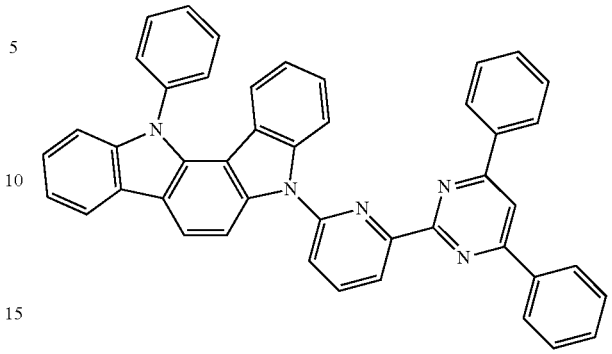
3-22
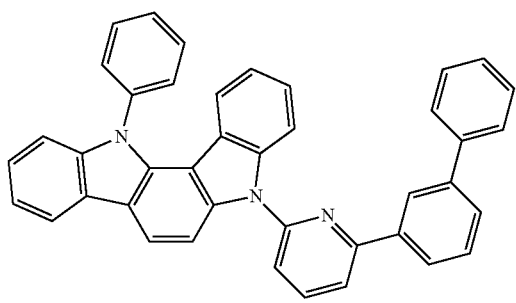
3-26
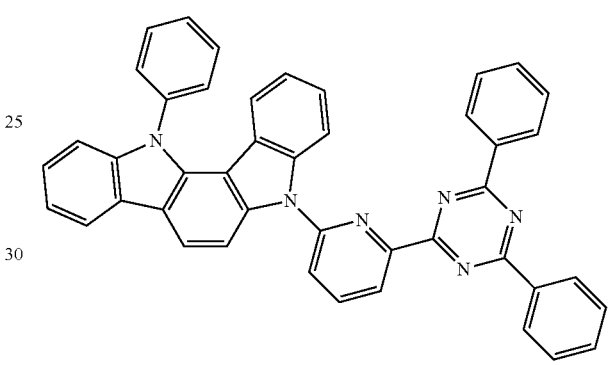
3-23
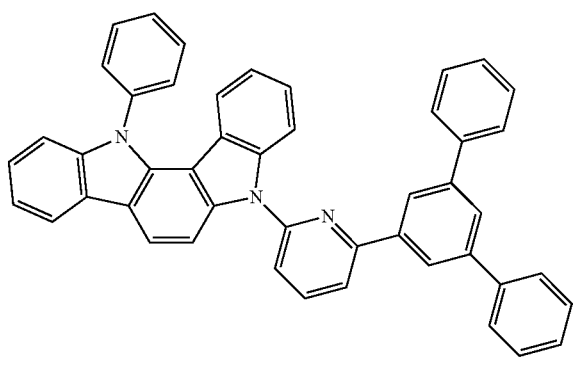
3-27
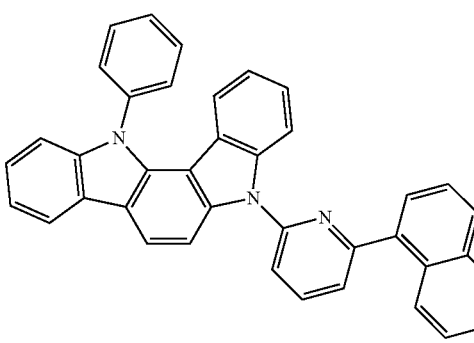
3-24
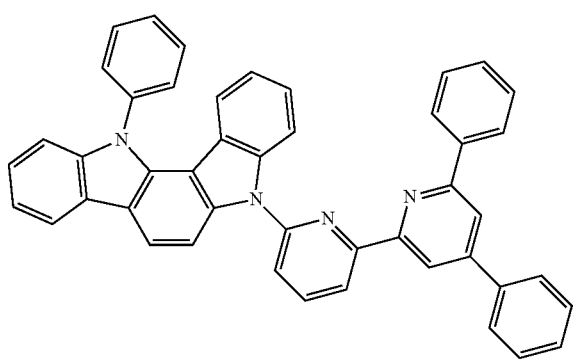
3-28
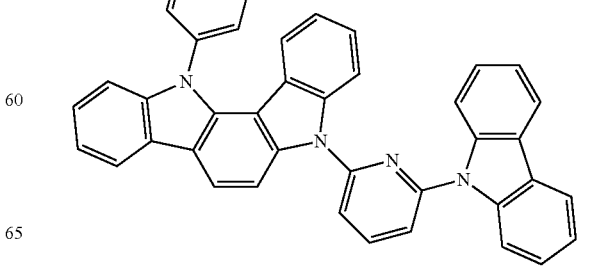

3-29
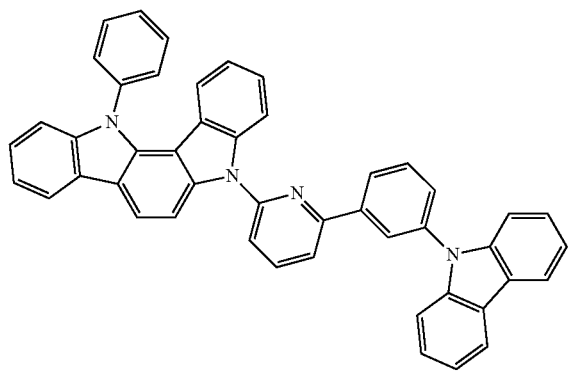
3-30
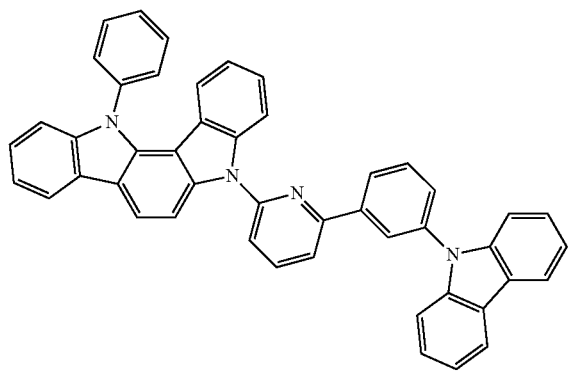
3-31
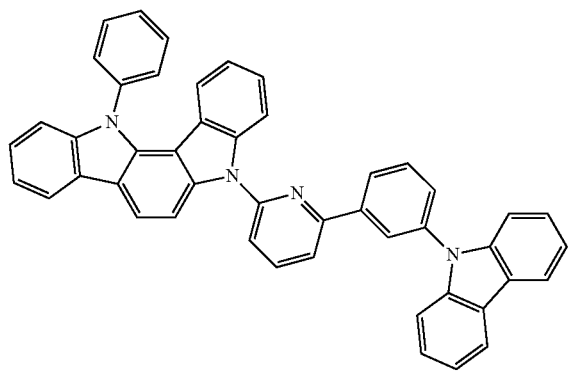
3-32
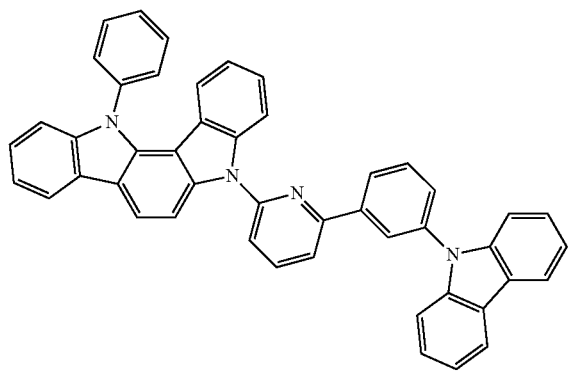
4-1
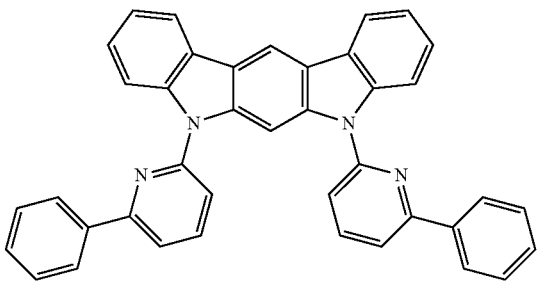
4-2
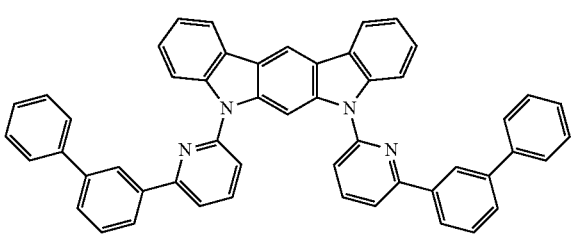
4-3
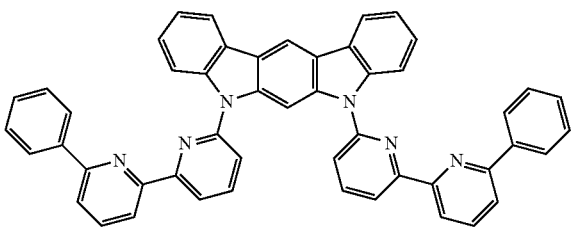
4-4
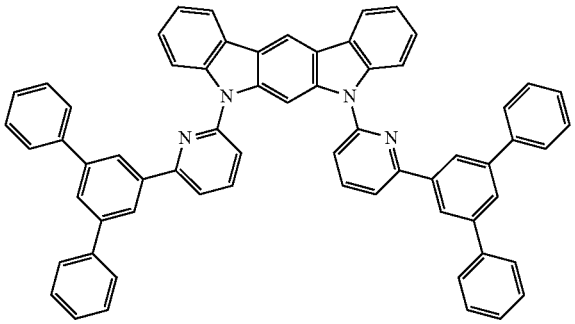
4-5
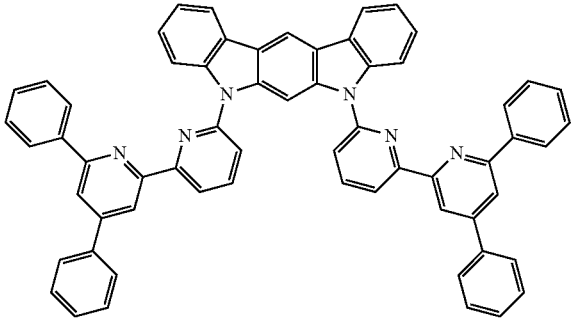

-continued
4-6
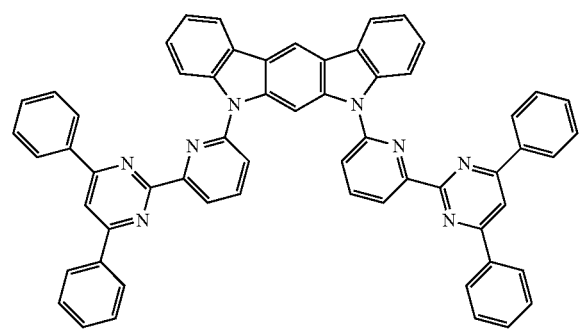
4-7
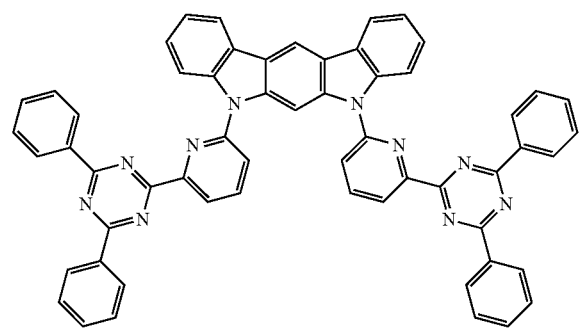
4-8
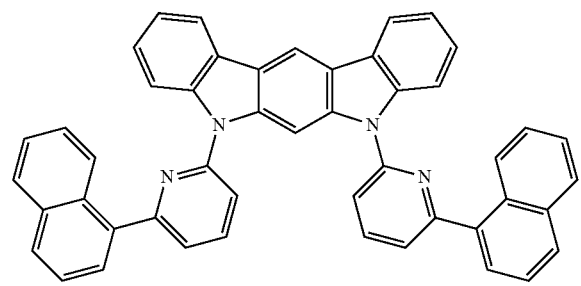
4-9
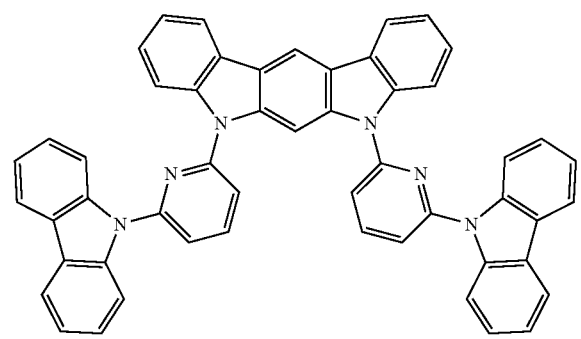
-continued
4-10
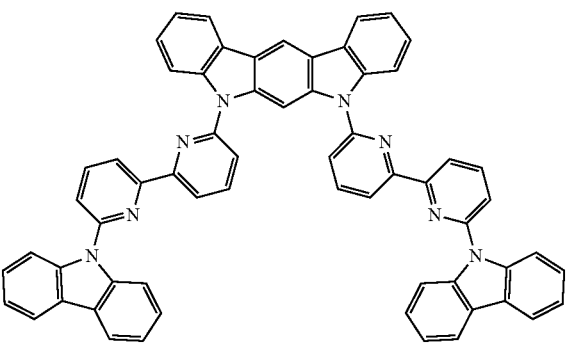
4-11
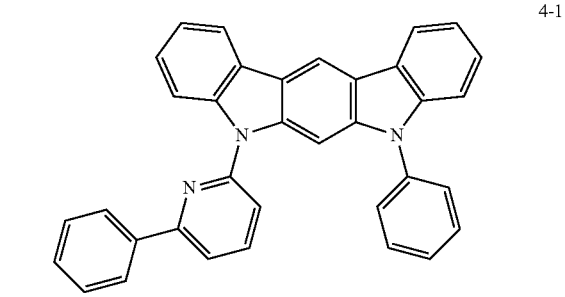
4-12
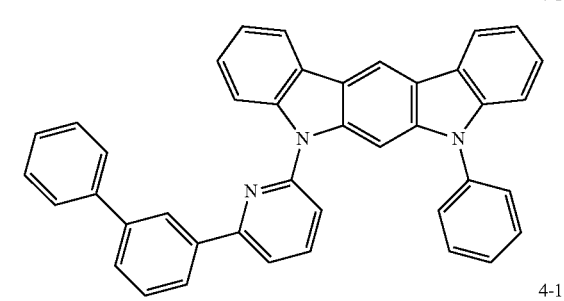
4-13
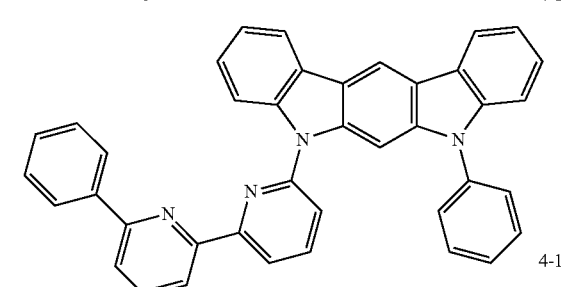
4-14
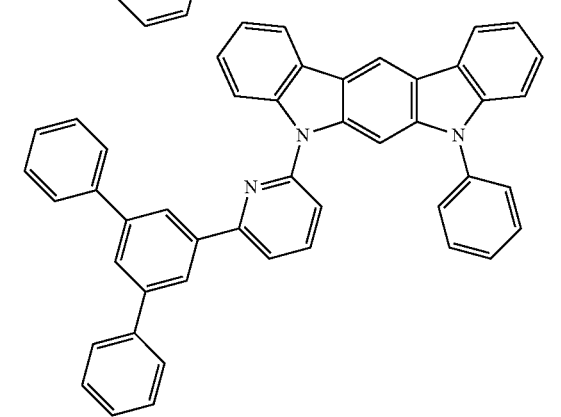

4-15
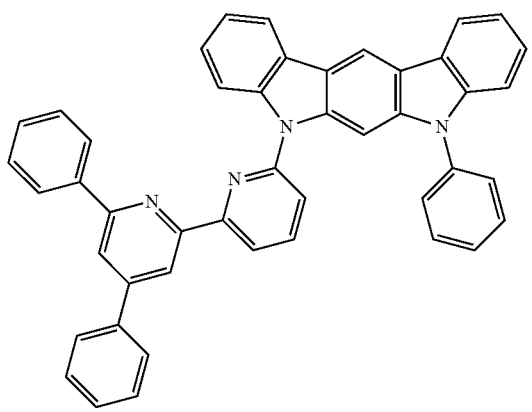
4-16
4-17
4-18
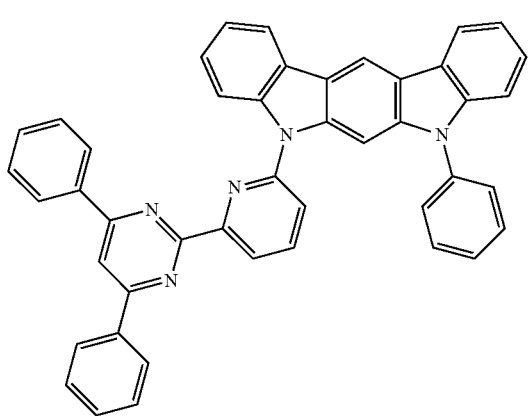
4-19
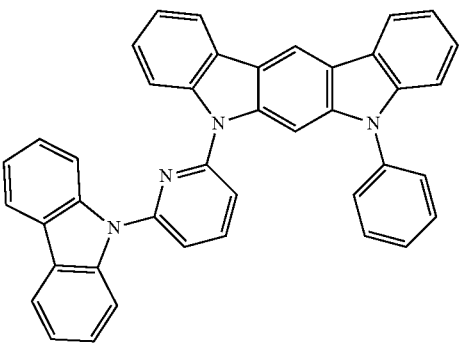
4-20
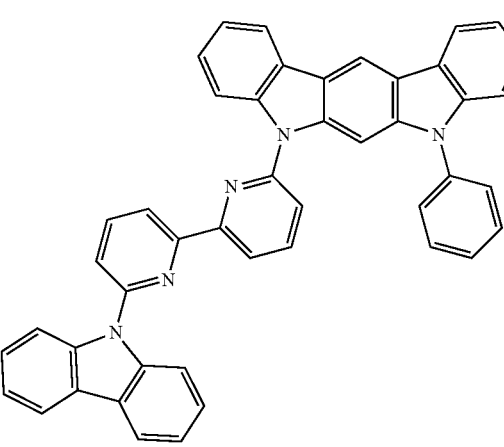
5-1
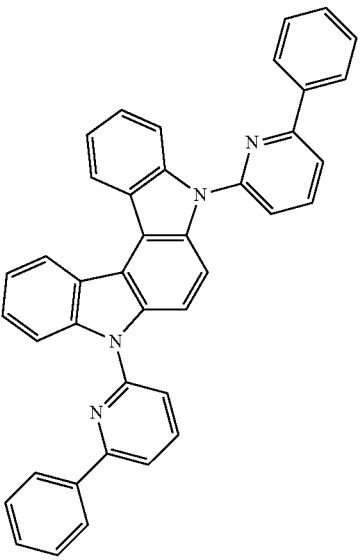

5-2
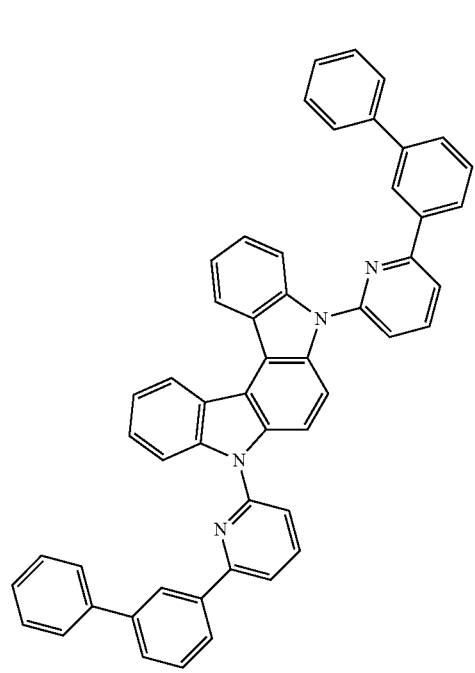
5-4
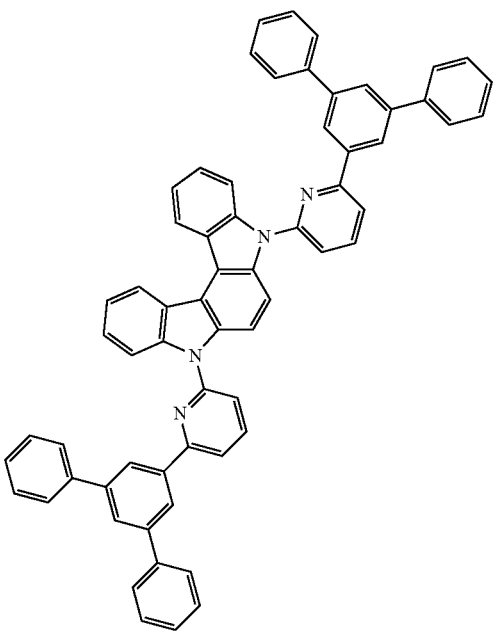
5-3
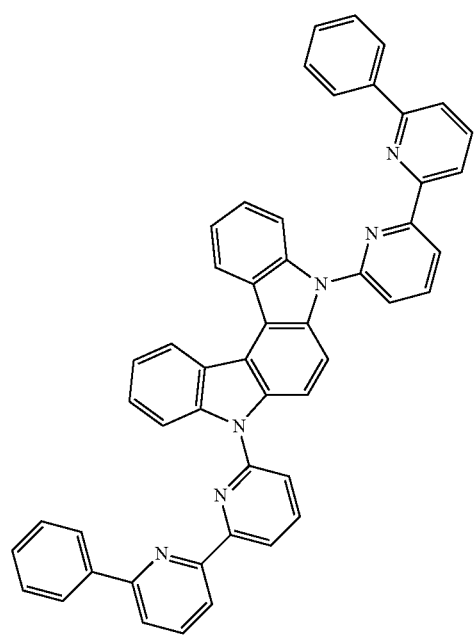
5-5
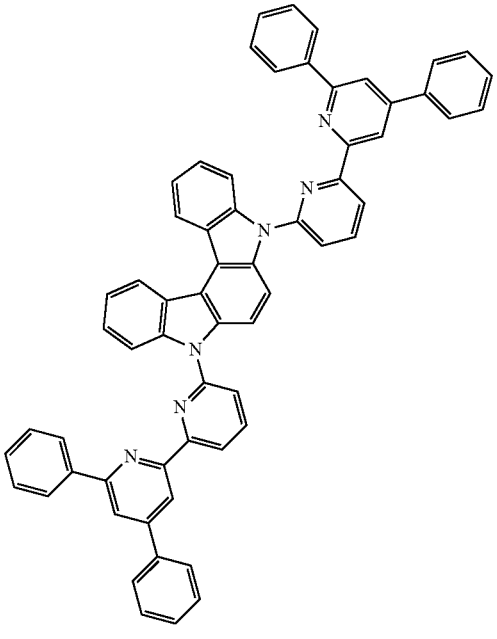

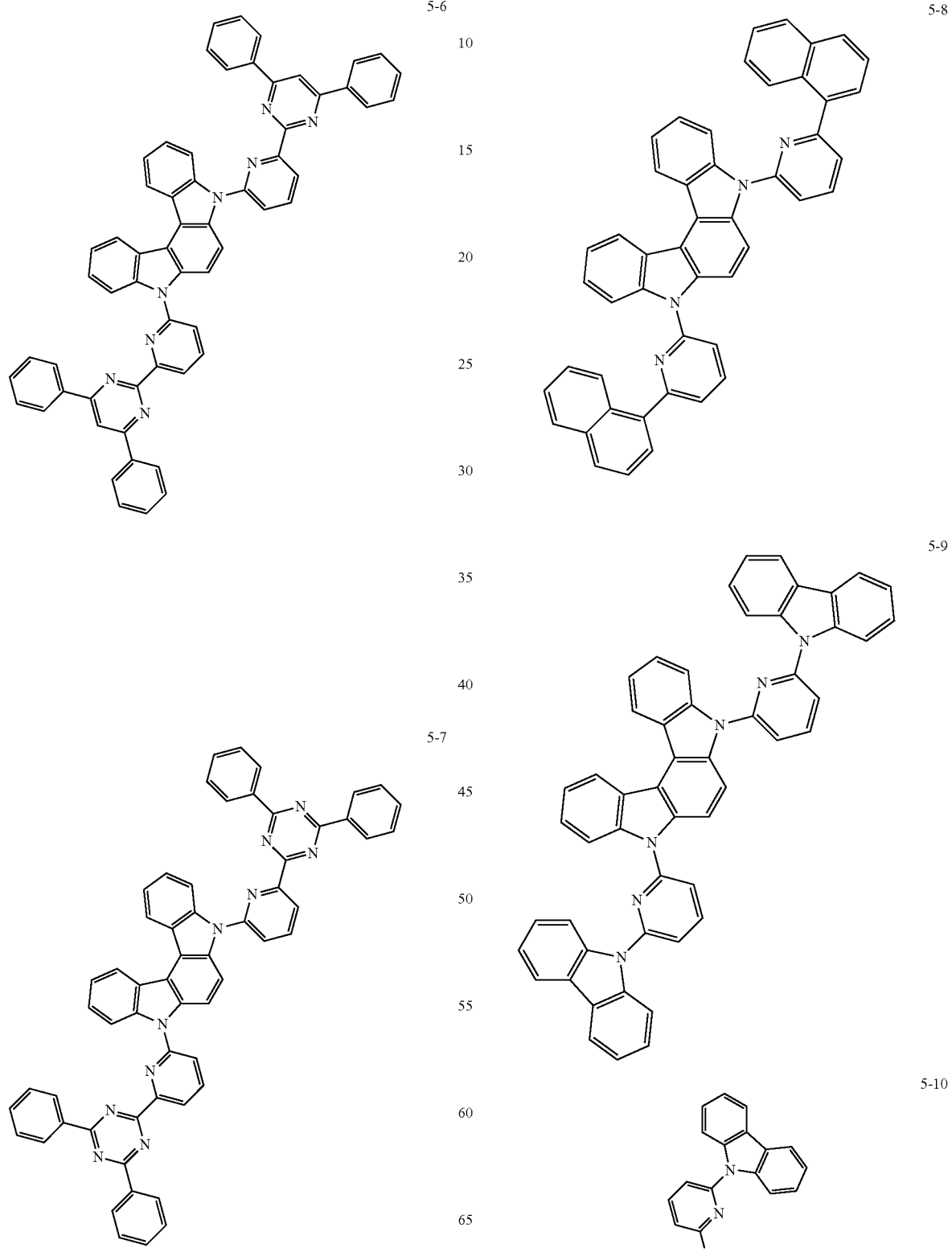

-continued
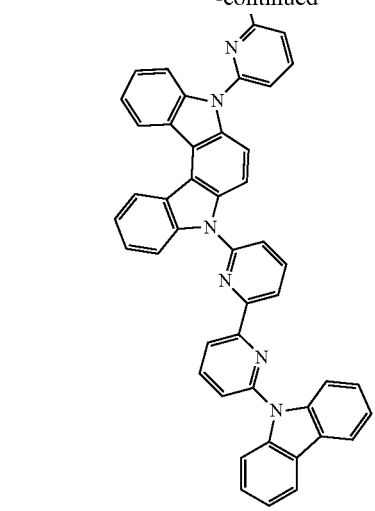
5-11
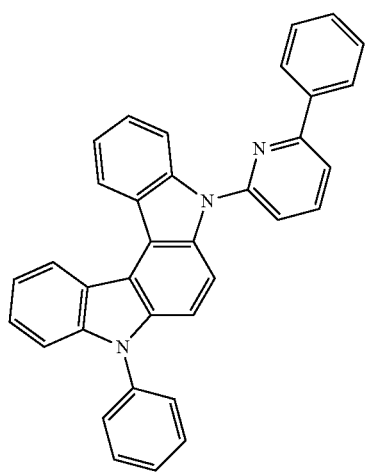
5-12
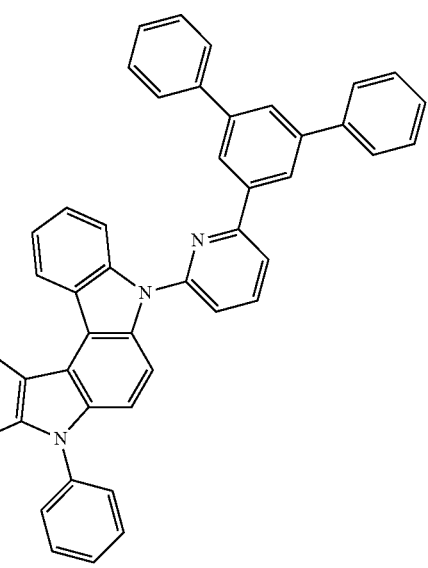
-continued
5-13
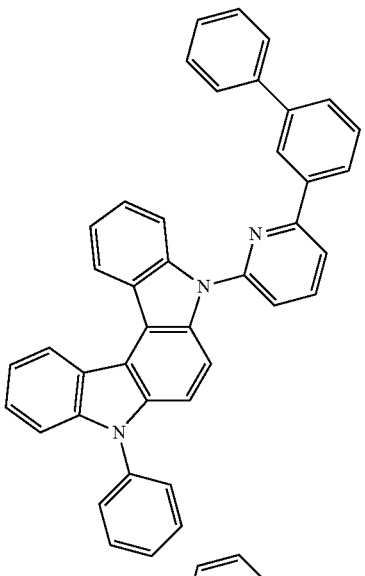
5-14
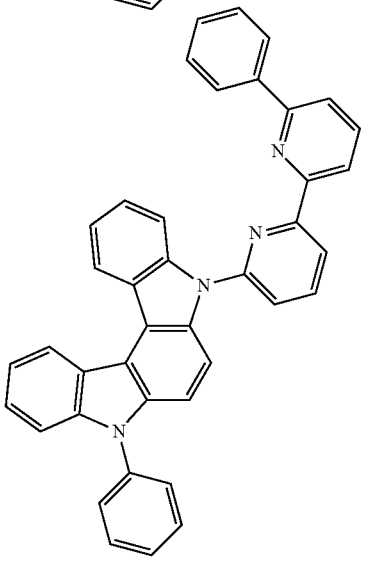
5-15
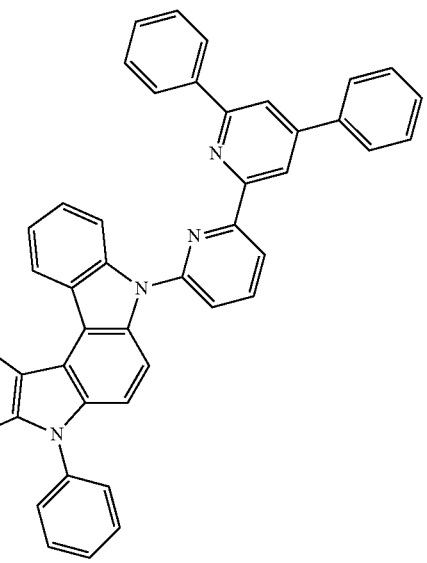

5-16

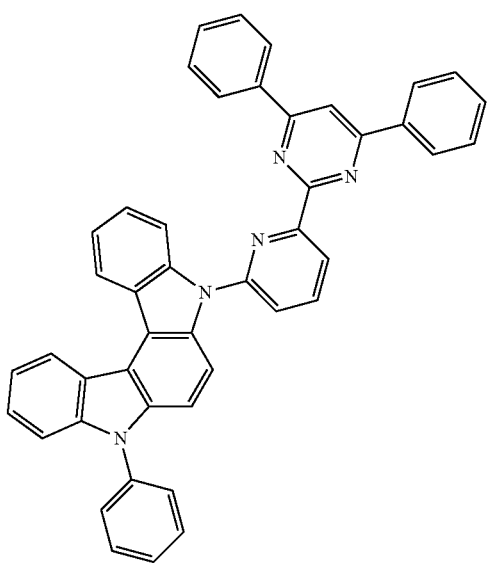

5-17

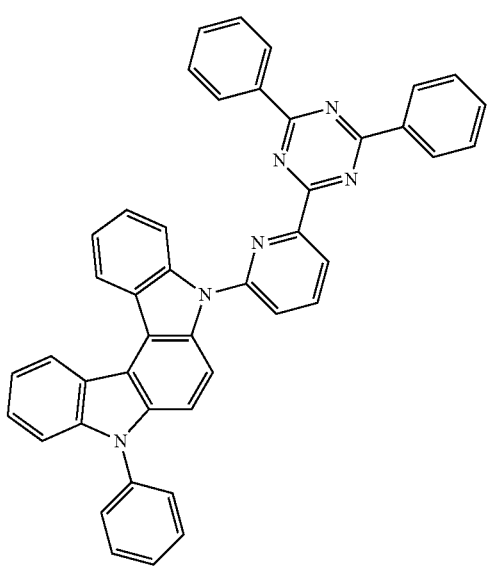

5-18

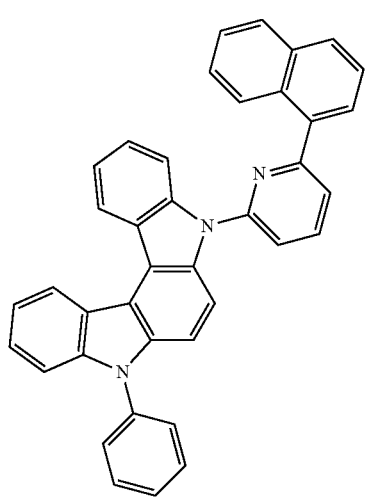

5-19

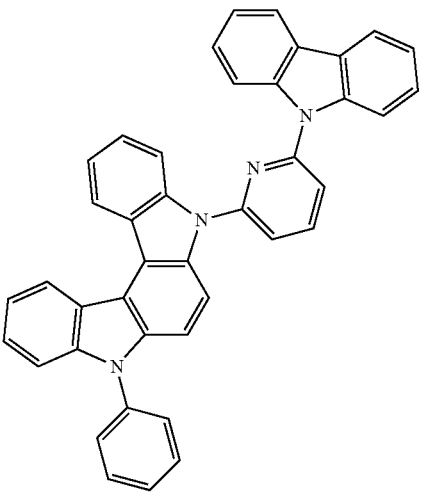

5-20

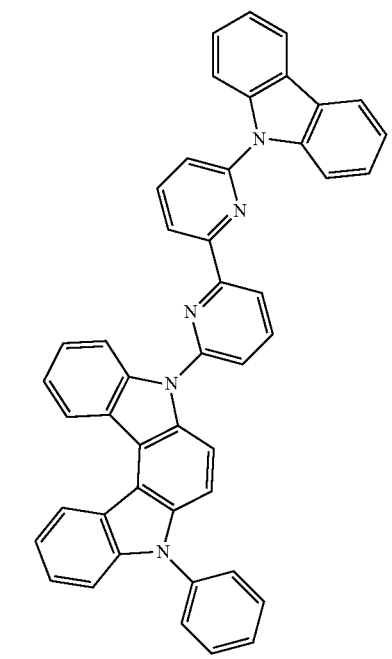

When the material for a phosphorescent light-emitting device of the present invention is contained in at least one of a plurality of organic layers of an organic EL device formed by laminating an anode, the plurality of organic layers, and a cathode on a substrate, an excellent organic electroluminescent device is provided. A light-emitting layer, a hole-transporting layer, an electron-transporting layer, or a hole-blocking layer is suitable as the organic layer in which the material for a phosphorescent light-emitting device is contained. It is more preferred that the material for a phosphorescent light-emitting device be contained as a host material in a light-emitting layer containing a phosphorescent light-emitting dopant.

Next, the organic EL device using the material for a phosphorescent light-emitting device of the present invention is described.

The organic EL device of the present invention has organic layers including at least one light-emitting layer between an anode and a cathode laminated on a substrate. In addition, at least one of the organic layers contains the material for a phosphorescent light-emitting device of the present invention. The material for a phosphorescent light-emitting device of the present invention is advantageously contained in the light-emitting layer together with a phosphorescent light-emitting dopant.

Next, the structure of the organic EL device of the present invention is described with reference to the drawings. However, the structure of the organic EL device of the present invention is by no means limited to one shown in the drawings.

FIG. 1 is a cross-sectional view showing a structural example of a general organic EL device used in the present invention. Reference numeral 1 denotes a substrate, 2 denotes an anode, 3 denotes a hole-injecting layer, 4 denotes a hole-transporting layer, 5 denotes a light-emitting layer, 6 denotes an electron-transporting layer, and 7 denotes a cathode. The organic EL device of the present invention may have an exciton-blocking layer adjacent to the light-emitting layer, or may have an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention has the substrate, the anode, the light-emitting layer, and the cathode as its essential layers. The organic EL device of the present invention preferably has a hole-injecting/transporting layer and an electron-injecting/transporting layer in addition to the essential layers, and more preferably has a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure compared with FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated if necessary.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a larger work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which maybe used for manufacturing an amorphous, transparent conductive film. In order to produce the anode, it may be possible to form any of those electrode substances into a thin film by using a method such as vapor deposition or sputtering and form a pattern having a desired design thereon by photolithography. Alternatively, in the case of not requiring high pattern accuracy (about 100 µm or more), a pattern may be formed via a mask having a desired design when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred Ω/□ or less. Further, the thickness of the resultant film is, depending on the material used, selected from usually the range of 10 to 1,000 nm, preferably the range of 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a smaller work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or sputtering. Further, the sheet resistance as the cathode is preferably several hundred Ω/□ or less, and the thickness of the resultant film is selected from usually the range of 10 nm to 5 µm, preferably the range of 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer is a phosphorescent light-emitting layer and includes a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold. Such organic metal complexes are known in the prior art documents and the like, and a complex is selected therefrom and may be used.

Preferred examples of the phosphorescent light-emitting dopant include complexes such as Ir(ppy)3, complexes such as Ir(bt)2·acac3, and complexes such as PtOEt3, the complexes each having a noble metal element such as Ir as a central metal. Specific examples of those complexes are shown below, but the complexes are not limited to the compounds described below.

55
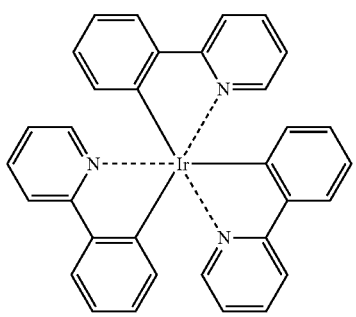
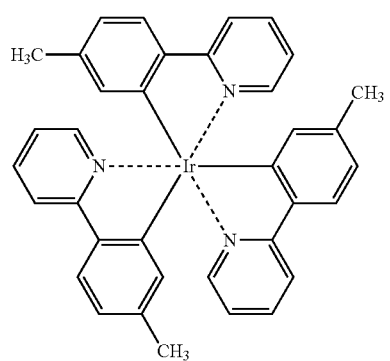
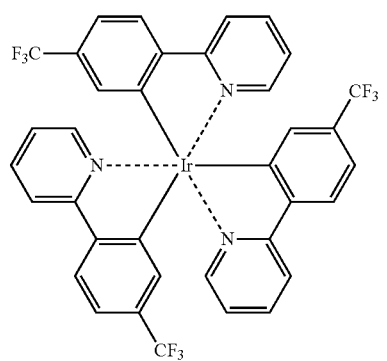
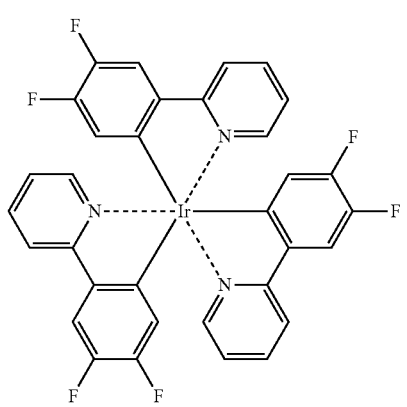
56
-continued
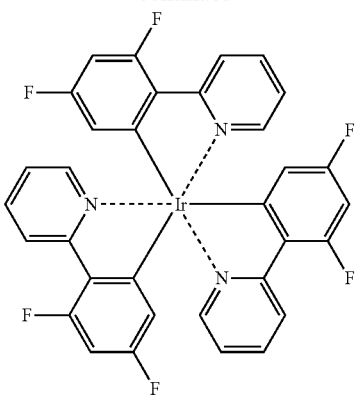
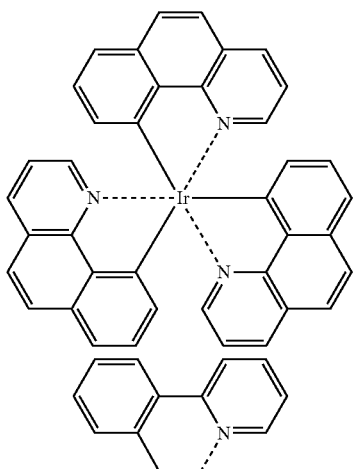
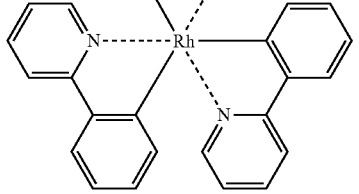
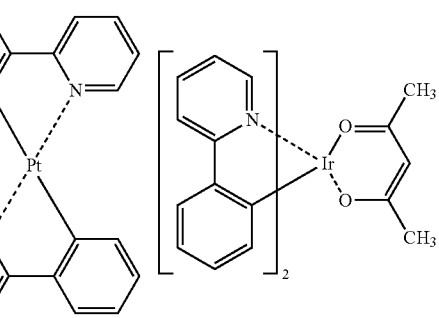
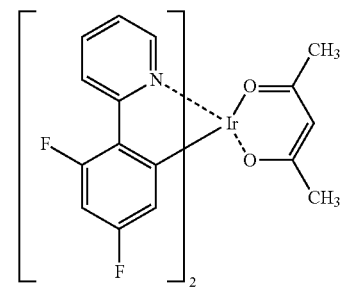

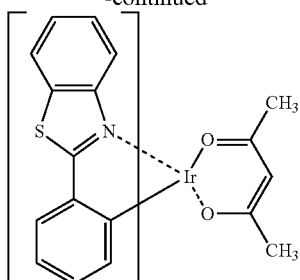
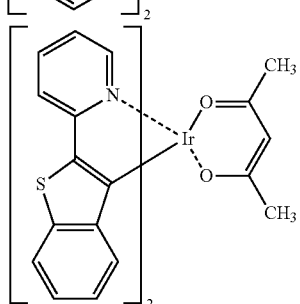
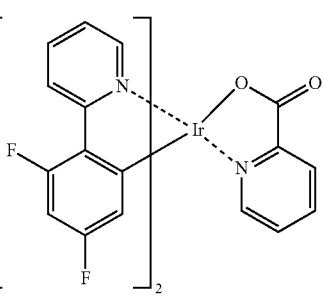
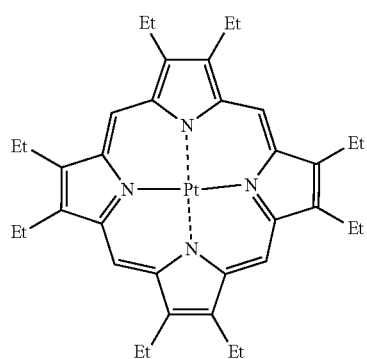
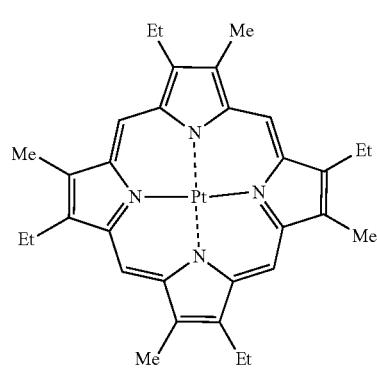
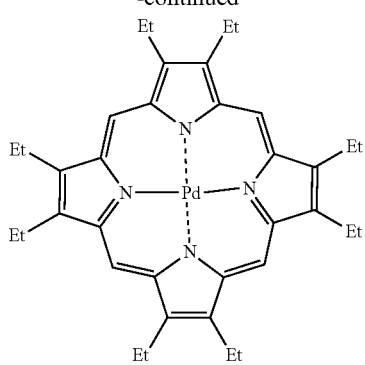
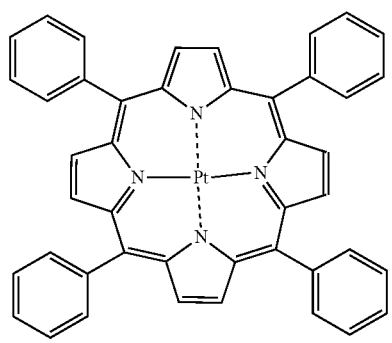
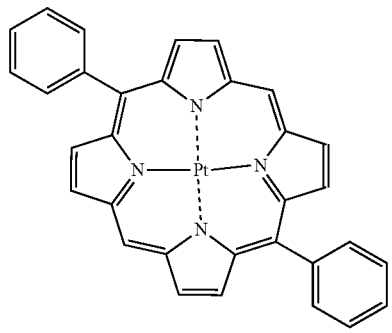
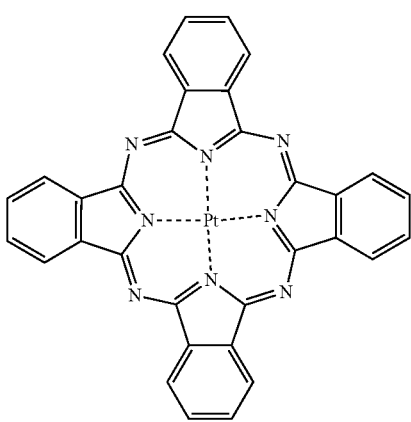

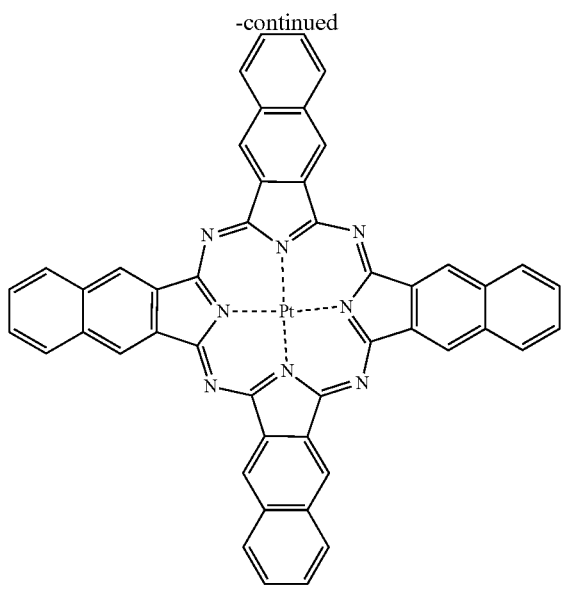

The content of the phosphorescent light-emitting dopant in the light-emitting layer is in the range of preferably 5 to 30 wt %.

It is preferred to use, as a host material in the light-emitting layer, an indolocarbazole compound represented by the general formula (1) according to the present invention. However, when the indolocarbazole compound is used in any of the organic layers other than the light-emitting layer, the host material to be used in the light-emitting layer may be another host material other than the indolocarbazole compound, or the indolocarbazole compound and any other host material may be used in combination. Further, a plurality of kinds of known host materials may be used in combination.

It is preferred to use, as a usable known host compound, a compound that has a hole-transporting ability and an electron-transporting ability, is capable of preventing luminescence from having a longer wavelength, and has a higher glass transition temperature.

Such other host materials are known because they are mentioned in many patent literatures and the like, and hence a suitable host material may be chosen from those in the patent literatures and the like. Specific examples of the host material, which are not particularly limited, include an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrine-based compound, an anthraquinodimethane derivative, an anthrone derivative, a diphenylquincne derivative, a thiopyrane dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a polyphenylene derivative, a polyphenylene vinylene derivative, and a polyfluorene derivative.

—Injecting layer—

The injecting layer refers to a layer provided between an electrode and an organic layer for the purpose of lowering a driving voltage and improving a light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be provided as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use an indolocarbazole compound represented by the general formula (1) according to the present invention for the hole-blocking layer. However, when the indolocarbazole compound is used in any of the organic layers other than the hole-blocking layer, a known material for a hole-blocking layer may be used. Further, it is possible to use, as a material for the hole-blocking layer, any of the below-mentioned materials for the electron-transporting layer as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

It is possible to use, as a material for the electron-blocking layer, any of the below-mentioned materials for the hole-transporting layer as required. The thickness of the electron-blocking layer is preferably 3 to 100 nm, more preferably 5 to 30 nm.

—Exciton-Blocking Layer—

The exciton-blocking layer refers to a layer used for blocking excitons produced by the recombination of a hole and an electron in the light-emitting layer from diffusing in charge-transporting layers. Inserting this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

A material for the exciton-blocking layer is exemplified by 1,3-dicarbazolylbenzene (mCP) and bis(2-methyl-8-quinolinolato)-4-phenylphenolatoaluminum (III) (BAlq).

—Hole-Transporting Layer—

The hole-transporting layer is formed of a hole-transporting material having a function of transporting holes, and a single hole-transporting layer or a plurality of hole-transporting layers may be provided.

The hole-transporting material has hole-injecting property or hole-transporting property or has electron-blocking property, and any of an organic compound and an inorganic compound may be used as the hole-transporting material. It is preferred to use a material represented by the general formula (1) according to the present invention for the hole-transporting layer. However, it is possible to select and use any compound from conventionally known compounds. Examples of the known hole-transporting material which may be used include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive polymeric oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be provided.

It is recommended that an electron-transporting material (which also serves as a hole-blocking material in some cases) have a function of transferring electrons injected from the cathode into the light-emitting layer. It is preferred to use a material represented by the general formula (1) according to the present invention for the electron-transporting layer. However, it is possible to select and use any compound from conventionally known compounds. Examples thereof include a nitro-substituted fluorene derivative, a diphenylquinone derivative, a thiopyran dioxide derivative, carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the above-mentioned oxadiazole derivative and a quinoxaline derivative which has a quinoxaline ring known as an electron withdrawing group. Further, it is also possible to use a polymer material in which any of those materials is introduced in a polymer chain or is used as a polymer main chain.

EXAMPLES

Hereinafter, the present invention is described in more detail with reference to examples, and the present invention is, as a matter of course, not limited to these examples. The present invention may be carried out in various forms as long as the various forms do not deviate from the gist of the present invention.

The routes described below were used to synthesize indolocarbazole compounds each serving as a material for a phosphorescent light-emitting device. It should be noted that the number of each compound corresponds to the number given to each chemical formula described above.

Synthesis Example 1

Synthesis of 11,12-dihydroindolo[2,3-a]carbazole (IC-1)

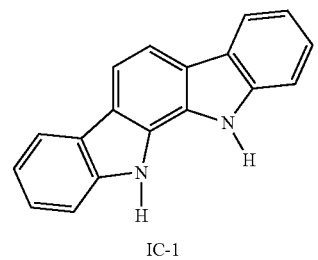

IC-1

Under a nitrogen atmosphere, 3.0 g (0.031 mol) of concentrated sulfuric acid were added dropwise over 5 minutes to 33.3 g (0.30 mol) of 1,2-cyclohexanedione, 86.0 g (0.60 mol) of phenylhydrazine hydrochloride, and 1,000 ml of ethanol with stirring at room temperature. After that, the mixture was stirred for 4 hours while being heated at 65° C. The reaction solution was cooled to room temperature. The precipitated crystal was then collected by filtration and washed with ethanol (2×500 ml) to afford 80.0 g of a purple-brown crystal. 72.0 g (0.26 mol) of the crystal, 72.0 g of trifluoroacetic acid, and 720.0 g of acetic acid were stirred for 15 hours while being heated at 100° C. The reaction solution was cooled to room temperature. The precipitated crystal was then collected by filtration and washed with acetic acid (200 ml). The crystal was subjected to purification by reslurrying to afford 30.0 g (45% yield) of IC-1 as a white crystal.

Synthesis Example 2

Synthesis of 5,12-dihydroindolo[3,2-a]carbazole (IC-2)

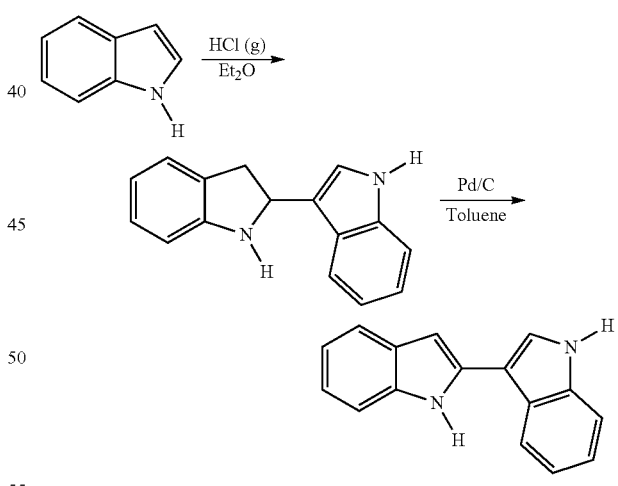

A

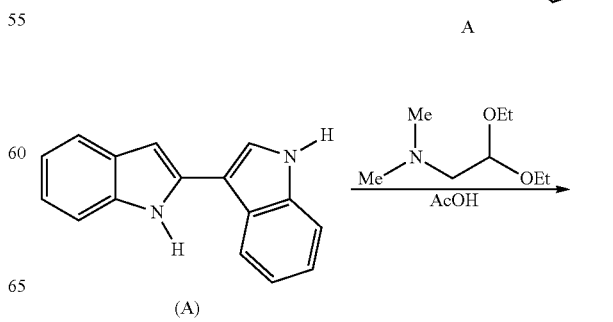

(A)

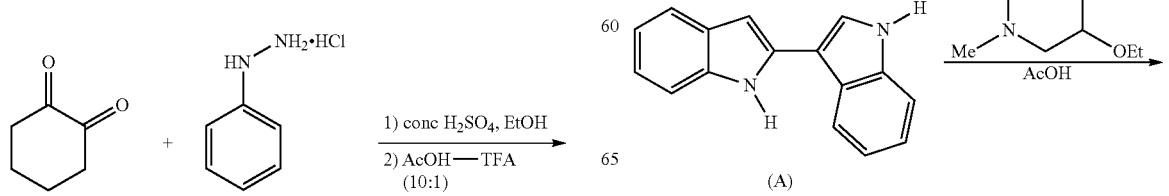

-continued

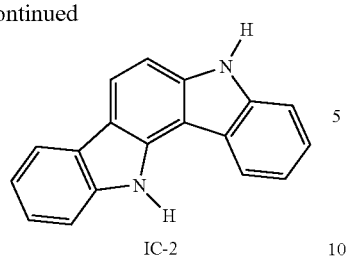

IC-2

Under a nitrogen atmosphere, a hydrogen chloride gas produced by adding dropwise 112.0 g (1.10 mol) of concentrated hydrochloric acid to 211.7 g (2.16 mol) of concentrated sulfuric acid over 1 hour was blown into a solution of 20.0 g (0.17 mol) of indole in 300 ml of dry diethyl ether, while the solution was being stirred at room temperature. After the reaction solution was stirred at room temperature for 15 hours, 121.0 g of ethyl acetate and 303.2 g of a saturated sodium hydrogen carbonate aqueous solution were added. After the aqueous layer in the mixture was extracted with ethyl acetate (2×100 ml), the organic layer was washed with a saturated sodium hydrogen carbonate aqueous solution (100 ml) and distilled water (2×100 ml). The organic layer was dried over anhydrous magnesium sulfate. The magnesium sulfate was then separated by filtration and the solvent was subjected to vacuum distillation. The resultant residue was dissolved in 150 ml of toluene, and 2.5 g of palladium/activated carbon were added. Then, the mixture was stirred for 3 hours while being heated at 111° C. to reflux. The reaction solution was cooled to room temperature, followed by filtration of the palladium/activated carbon and vacuum distillation of the solvent. The resultant was purified by recrystallization to afford 14.7 g (37% yield) of an intermediate A as a white crystal.

Under a nitrogen atmosphere, 14.1 g (0.061 mol) of the intermediate A, 11.4 g (0.071 mol) of N,N'-dimethylaminoacetaldehyde diethyl acetal, and 110.0 g of acetic acid were stirred for 8 hours while being heated at 118° C. to reflux. After the reaction solution was cooled to room temperature, the precipitated crystal was collected by filtration and washed with acetic acid (30 ml). The resultant crystal was subjected to purification by reslurrying to afford 10.4 g (67% yield) of IC-2 as a white crystal.

Example 1

Synthesis of Compound 1-19

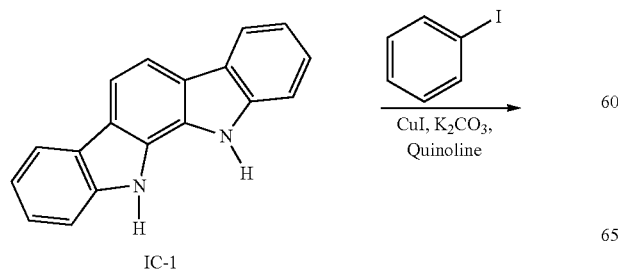

-continued

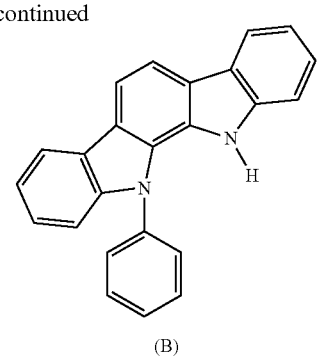

(B)

Under a nitrogen atmosphere, 26.0 g (0.10 mol) of IC-1, 122.7 g (0.60 mol) of iodobenzene, 54.7 g (0.29 mol) of copper iodide, 66.7 g (0.48 mol) of potassium carbonate, and 800 ml of quinoline were stirred for 72 hours while being heated at 190° C. The reaction solution was cooled to room temperature. After that, distilled water (500 ml) and dichloromethane (500 ml) were then added while being stirred. The precipitated crystal was separated by filtration. The organic layer was then washed with distilled water (3×500 ml). The organic layer was dried over anhydrous magnesium sulfate. The magnesium sulfate was then separated by filtration and the solvent was subjected to vacuum distillation. The resultant residue was purified by silica gel column chromatography to afford 13.7 g (41% yield) of an intermediate B as a white solid.

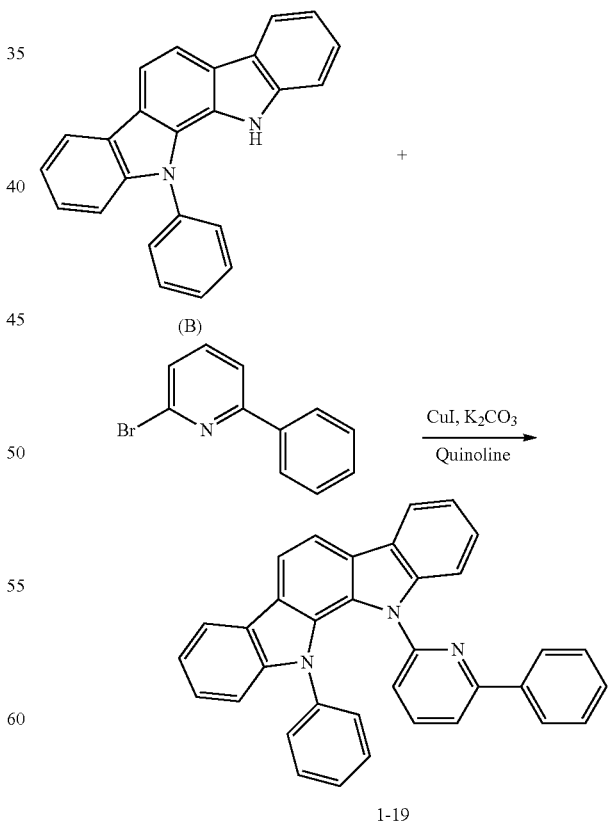

1-19

Figure 2:
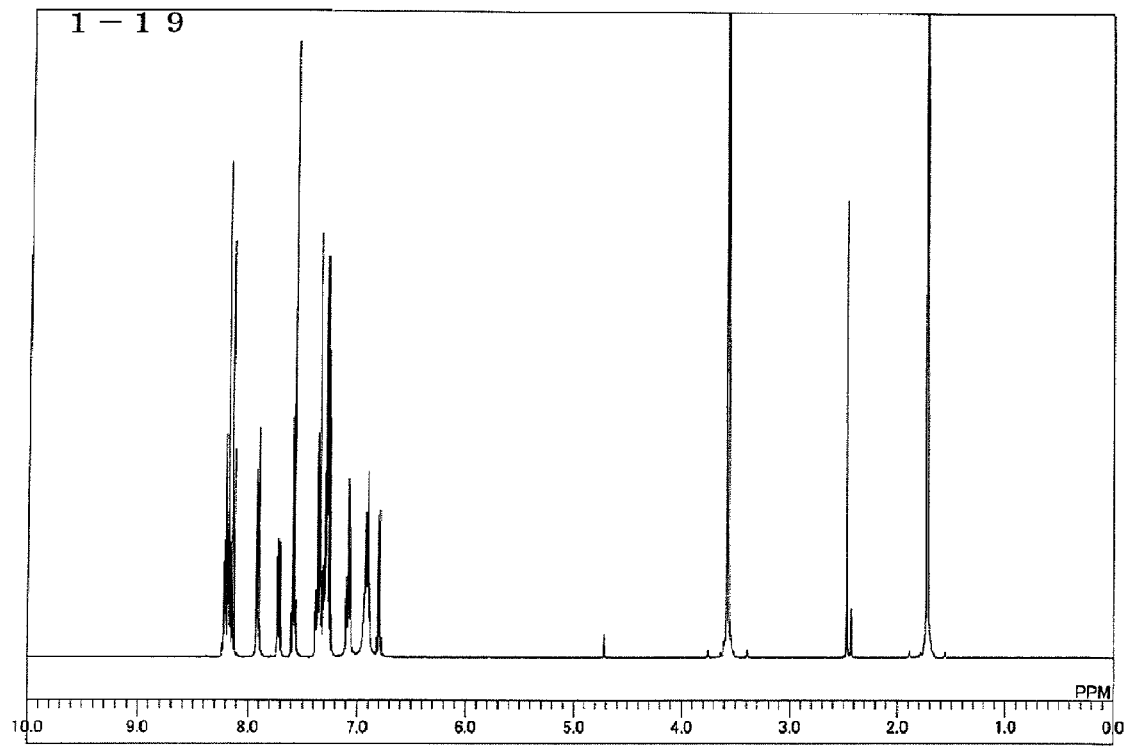
FIG. 2 shows a $^1$H-NMR chart of Compound 1-19 of the present invention.

Under a nitrogen atmosphere, 1.00 g (0.0030 mol) of the intermediate B, 0.70 g (0.0030 mol) of 2-bromo-6-phenylpyridine, 1.14 g (0.0060 mol) of copper iodide, 1.24 g (0.0090 mol) of potassium carbonate, and 50 ml of quinoline were stirred for 20 hours while being heated at 190° C. After 20 hours, a mixed solution obtained by dissolving 0.30 g (0.0013 mol) of 2-bromo-6-phenylpyridine in 10 ml of quinoline was additionally charged and the mixture was stirred at 190° C. for 6 hours. The reaction solution was cooled to room temperature. After that, distilled water (200 ml) and dichloromethane (300 ml) were then added while being stirred. The precipitated crystal was separated by filtration. The organic layer was then washed with distilled water (3×200 ml). The organic layer was dried over anhydrous magnesium sulfate. The magnesium sulfate was then separated by filtration and the solvent was subjected to vacuum distillation. The resultant residue was purified by silica gel column chromatography to afford 0.39 g (0.00081 mol, 27% yield) of Compound 1-19 as a white solid. APCI-TOFMS, m/z 486 [M+H]⁺. FIG. 2 shows ¹H-NMR measurement results (measurement solvent: THF-d8).

Example 2

Synthesis of Compound 1-43

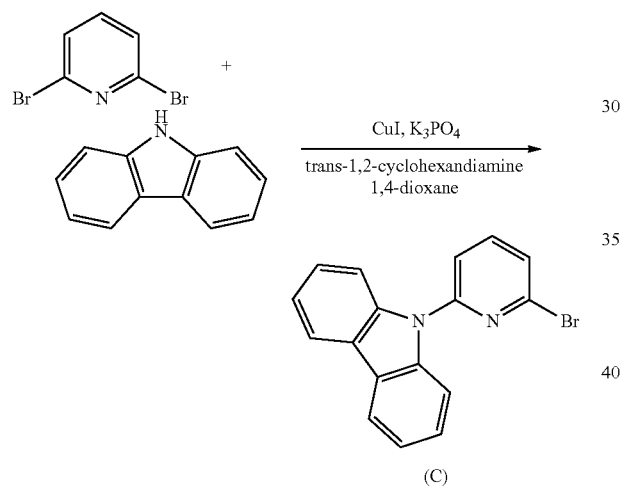

Under a nitrogen atmosphere, 50 g (0.21 mol) of 2,6-dibromopyridine, 17.5 g (0.10 mol) of carbazole, 0.53 g (0.0028 mol) of copper iodide, 116.2 g (0.55 mol) of tripotassium phosphate, and 1,000 ml of 1,4-dioxane were added and the mixture was stirred. To the resultant were added 3.5 g (0.031 mol) of trans-1,2-cyclohexanediamine and the mixture was heated to 110° C. and stirred for 4 hours. The reaction solution was cooled to room temperature. After that, inorganic matter was separated by filtration and the solvent was subjected to vacuum distillation. The resultant residue was dissolved in 300 ml of dichloromethane, 100 ml of distilled water were added thereto to separate an organic layer from an aqueous layer, and the organic layer was washed with distilled water (2×200 ml). The organic layer was dried over magnesium sulfate, the magnesium sulfate was separated by filtration, and the solvent was subjected to vacuum distillation. The resultant yellow crystal was dried under reduced pressure, and was then purified by column chromatography to afford a white powder. The powder was purified by recrystallization to afford 17.0 g (0.053 mol, 31% yield) of an intermediate C as a white powder.

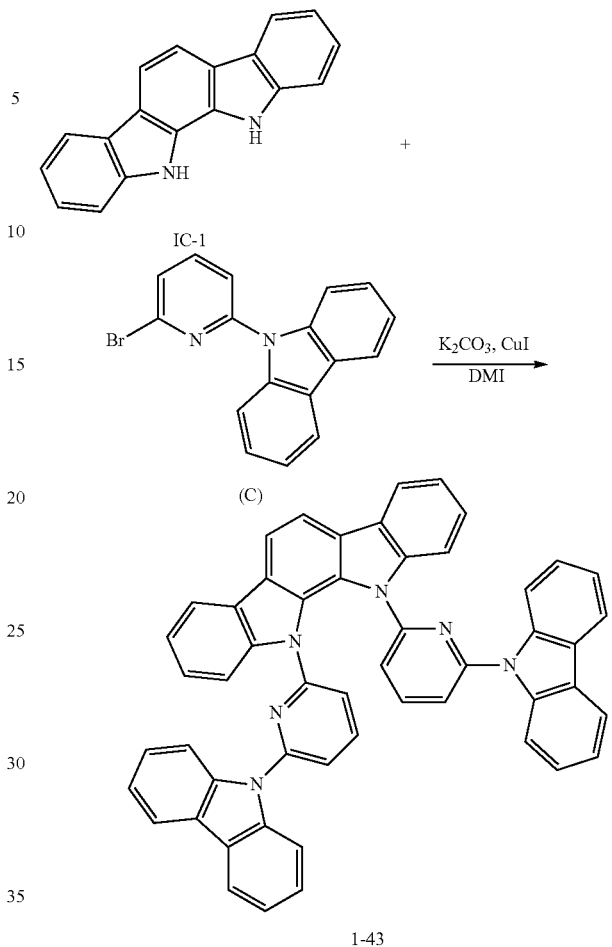

Under a nitrogen atmosphere, 2.5 g (0.0098 mol) of IC-1, 12.6 g (0.039 mol) of the intermediate C, 8.4 g (0.044 mol) of copper iodide, 10.1 g (0.073 mol) of potassium carbonate, and 150 ml of 1,3-dimethylimidazolidinone were stirred for 40 hours while being heated at 170° C. The reaction solution was cooled to room temperature, and inorganic matter was then separated by filtration. The filtrate was added to 1,000 ml of water and the mixture was stirred, followed by filtration of the precipitated crystal. The crystal was dried under reduced pressure and was then purified by column chromatography to afford 2.9 g (0.0039 mol, 40.0% yield) of Compound 1-43 as a white powder.

Figure 3:
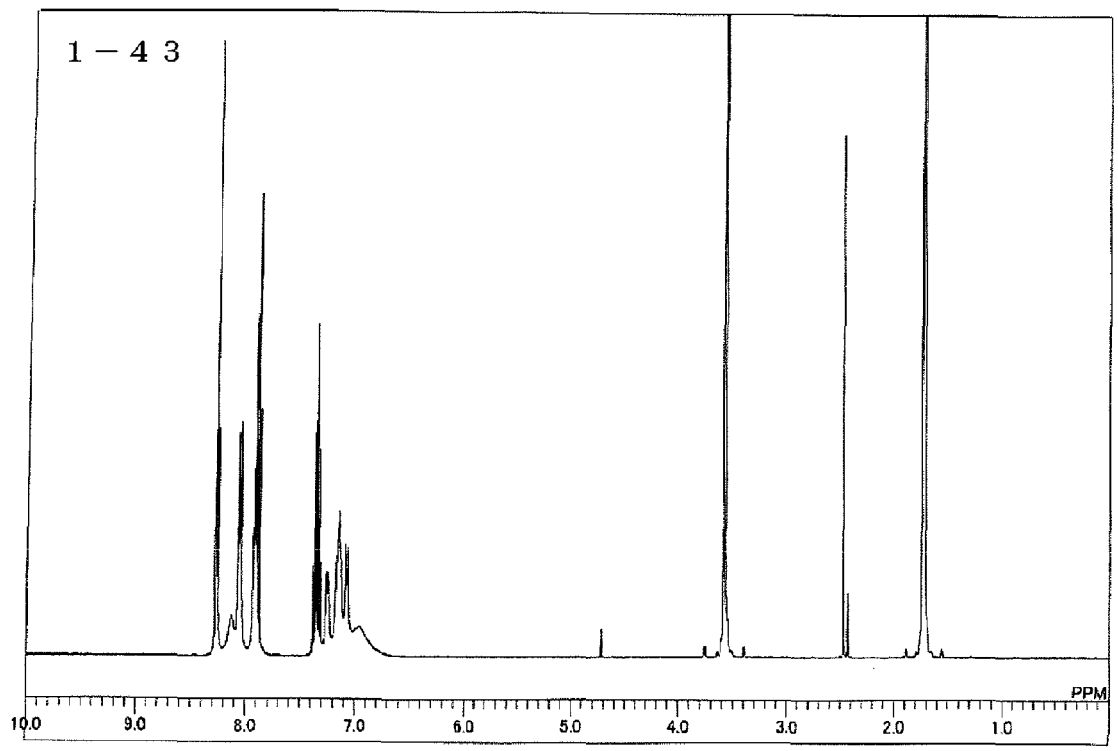
FIG. 3 shows a $^1$H-NMR chart of Compound 1-43 of the present invention.

APCI-TOFMS, m/z 741 [M+H]⁺. FIG. 3 shows ¹H-NMR measurement results (measurement solvent: THF-d8).

Example 3

Synthesis of Compound 3-11

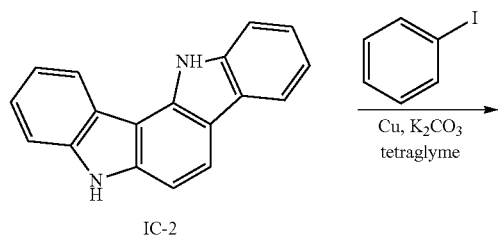

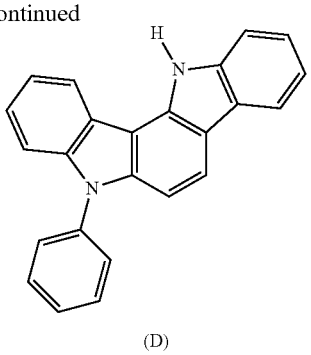

(D)

Figure 4:
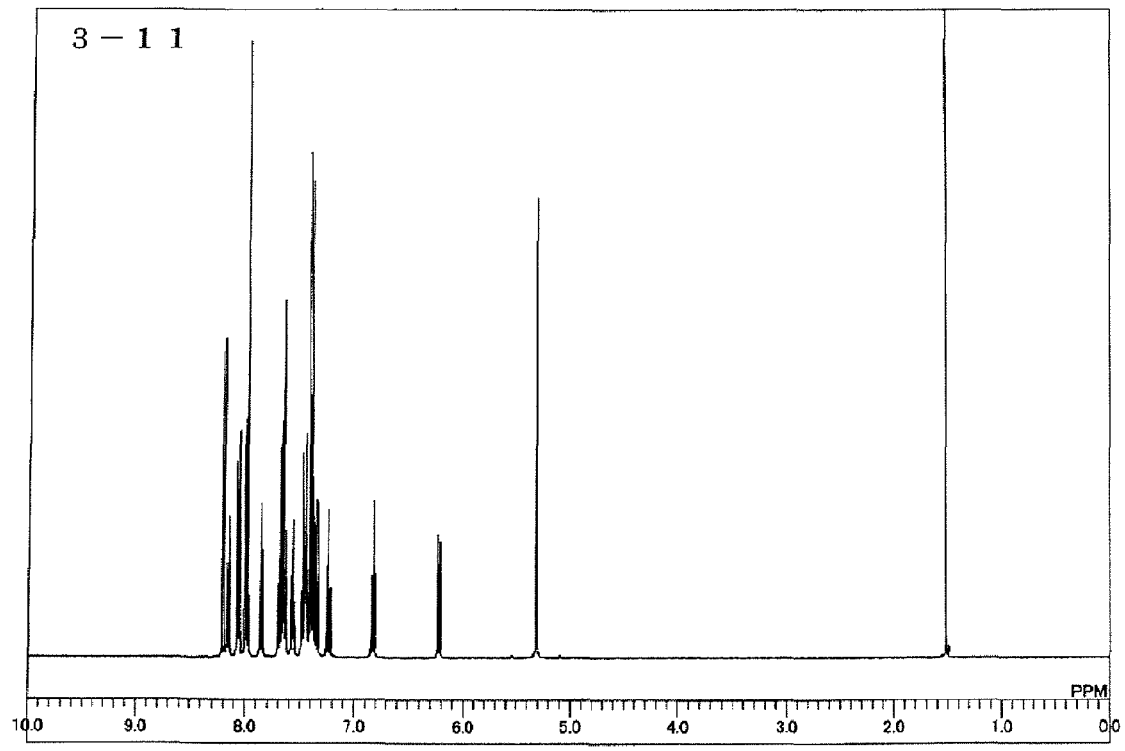
FIG. 4 shows a $^1$H-NMR chart of Compound 3-11 of the present invention.

Under a nitrogen atmosphere, 10.0g (0.039 mol) of IC-2, 39.8 g (0.20 mol) of iodobenzene, 6.2 g (0.098 mol) of copper, 8.1 g (0.059 mol) of potassium carbonate, and 200 ml of tetraglyme were added and the mixture was stirred. The mixture was then heated to 190° C. and stirred for 24 hours. The reaction solution was cooled to room temperature, and copper and inorganic matter were then separated by filtration. 200 ml of distilled water were added to the filtrate and the mixture was stirred, followed by filtration of the precipitated crystal. The crystal was dried under reduced pressure and was then purified by column chromatography to afford 9.7 g (0.029 mol, 75.0% yield) of an intermediate D as a white powder.

ridine, 4.2 g (0.065 mol) of copper, 16.6 g (0.12 mol) of potassium carbonate, and 250 ml of 1,3-dimethyl-2-imidazolidinone (DMI) were added and the mixture was heated to 200° C. and stirred for 4 days. The reaction solution was cooled to room temperature. After that, inorganic matter was separated by filtration. The filtrate was added dropwise to 1,000 ml of distilled water and the mixture was stirred overnight. The precipitated crystal was collected by filtration. The crystal collected by filtration was dissolved in 300 ml of dichloromethane, 100 ml of distilled water were added thereto to separate an organic layer from an aqueous layer, and the organic layer was washed with distilled water (2×200 ml). The organic layer was dried over magnesium sulfate, the magnesium sulfate was separated by filtration, and the solvent was subjected to vacuum distillation. The resultant viscous liquid was purified by column chromatography to afford a white powder. The powder was purified by recrystallization to afford 10.3 g (0.021 mol, 27% yield) of Compound 3-11 as a white powder. APCI-TOFMS, m/z 486 [M+H]$^+$. FIG. 4 shows $^1$H-NMR measurement results (measurement solvent: CD$_2$Cl$_2$).

Example 4

Synthesis of Compound 3-18

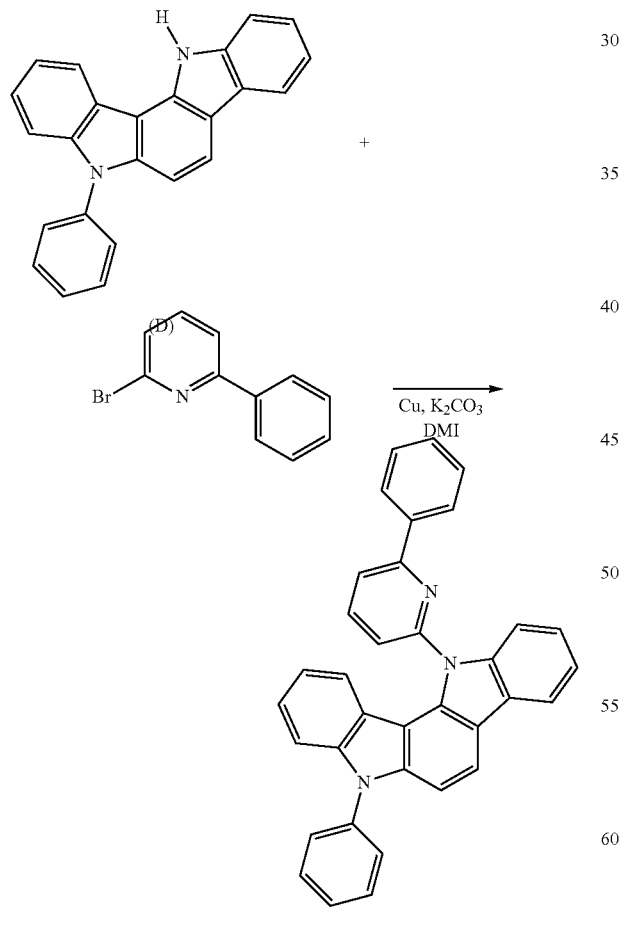

3-11

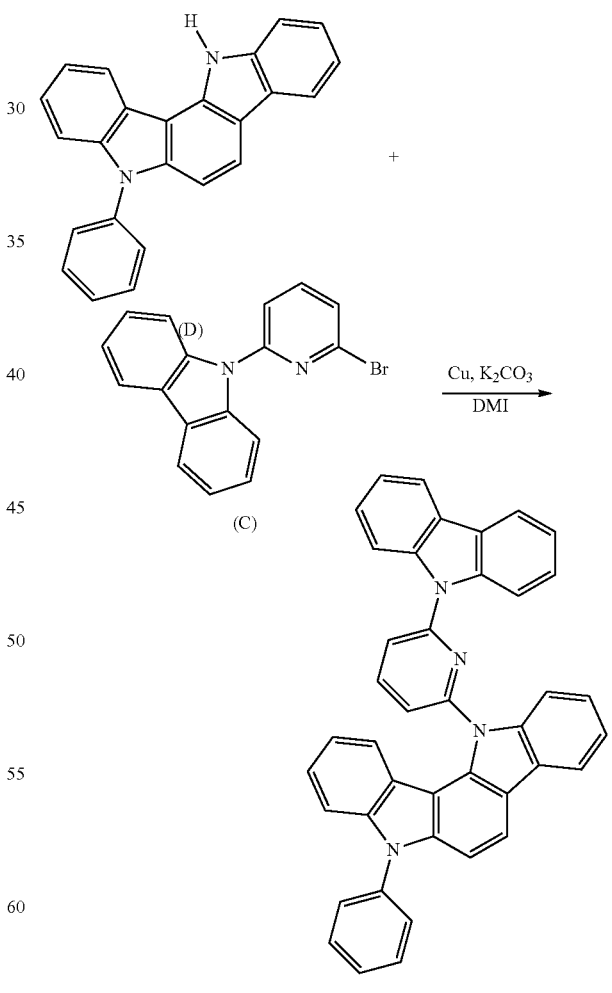

3-18

Under a nitrogen atmosphere, 26.0 g (0.078 mol) of the intermediate (D), 15.0 g (0.064 mol) of 2-bromo-6-phenylpy- Under a nitrogen atmosphere, 13.6 g (0.041 mol) of the intermediate D, 11.0 g (0.034 mol) of the intermediate C, 4.4 g (0.068 mol) of copper, 18.8 g (0.14 mol) of potassium carbonate, and 125 ml of 1,3-dimethyl-2-imidazolidinone (DMI) were added and the mixture was heated to 200° C. and stirred for 5 days. The reaction solution was cooled to room temperature. After that, inorganic matter was separated by filtration. The filtrate was added dropwise to 500 ml of distilled water in a conical flask and the mixture was stirred for 2 hours. The precipitated crystal was collected by filtration. The crystal collected by filtration was dissolved in 200 ml of dichloromethane, 100 ml of distilled water were added thereto to separate an organic layer from an aqueous layer, and the organic layer was washed with distilled water (2×100 ml). The organic layer was dried over magnesium sulfate, the magnesium sulfate was separated by filtration, and the solvent was subjected to vacuum distillation. The resultant viscous liquid was purified by column chromatography to afford 8.2 g (0.014 mol, 35% yield) of Compound 3-18 as a white powder.

Figure 5:
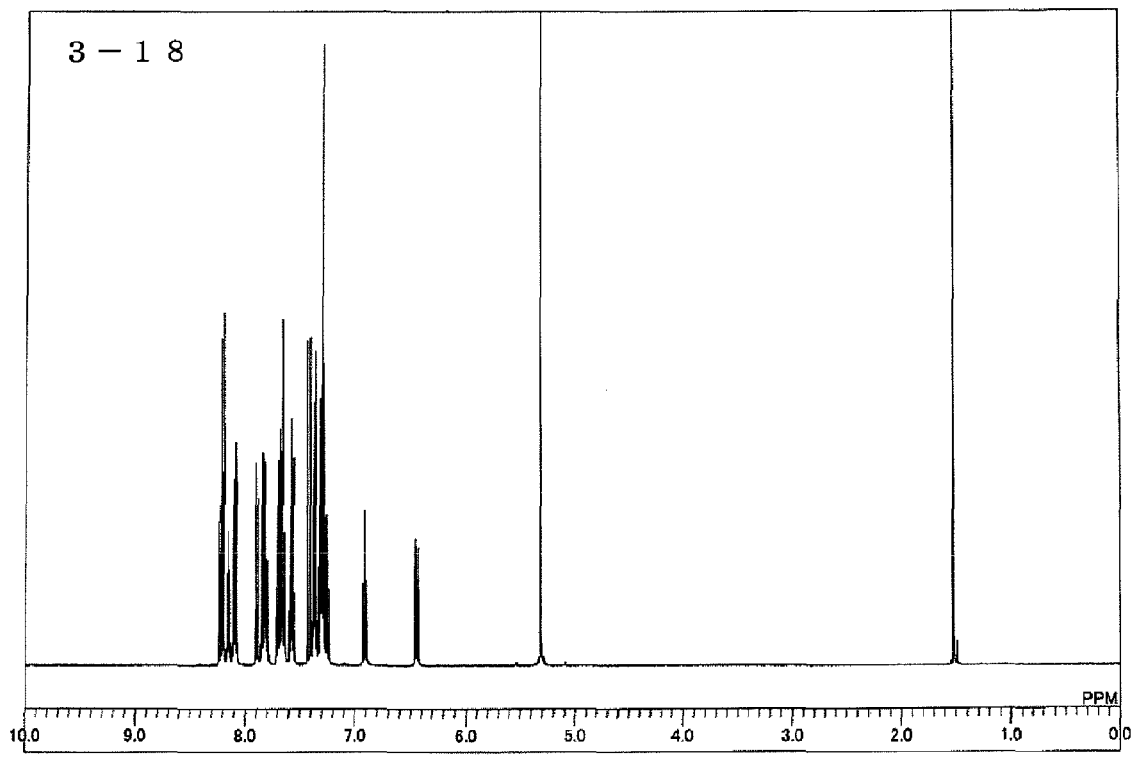
FIG. 5 shows a $^1$H-NMR chart of Compound 3-18 of the present invention.

APCI-TOFMS, m/z 575 [M+H]$^+$. FIG. 5 shows $^1$H-NMR measurement results (measurement solvent: $CD_2Cl_2$).

Further, Compounds 1-1, 2-1, 3-1, and 3-22 were synthesized according to the above-mentioned synthesis examples and the synthesis methods described herein, and they were used for manufacturing organic EL devices.

Example 5

On a glass substrate on which ITO had been formed into an anode having a film thickness of 150 nm, each thin film was laminated by using a vacuum deposition method at a vacuum degree of 4.0×10$^{-4}$ Pa. First, on the ITO film, copper phthalocyanine (CuPc) was formed into a film having a thickness of 20 nm. Next, 4,4'-bis [N-(1-naphthyl)-N-phenylamino]biphenyl (NPB) was formed into a film having a thickness of 40 nm as a hole-transporting layer. Next, on the hole-transporting layer, co-vapor deposition was carried out by using Exemplary Compound 1-1 as a host material for a light-emitting layer and tris(2-phenylpyridine)iridium (III) (Ir(ppy)3) as a guest material from different vapor deposition sources, forming a light-emitting layer having a thickness of 35 nm. In this case, the concentration of Ir(ppy)$_3$ was 7.0 wt %. Next, tris (8-hydroxyquinolinato)aluminum (III) (Alq3) was formed into a film having a thickness of 40 nm as an electron-transporting layer. Further, on the electron-transporting layer, lithium fluoride (LiF) was formed into a film having a thickness of 0.5 nm as an electron-injecting layer. Finally, on the electron-injecting layer, aluminum (Al) was formed into a film having a thickness of 170 nm as an electrode. Thus, an organic EL device was provided.

An external power source was connected to the resultant organic EL device, followed by application of a DC voltage. As a result, the organic EL device was found to have the luminescence properties shown in Table 1. In Table 1, the values of luminance, voltage, and luminous efficiency are those at 10 mA/cm$^2$. It should be noted that the maximum wavelength of the luminescence spectrum of the device is 517 nm, showing that luminescence is provided by Ir(ppy)$_3$.

Example 6

An organic EL device was manufactured in the same manner as that in Example 5 except that Compound 1-19 was used instead as the host material of the light-emitting layer.

Example 7

An organic EL device was manufactured in the same manner as that in Example 5 except that Compound 1-43 was used instead as the host material of the light-emitting layer.

Example 8

An organic EL device was manufactured in the same manner as that in Example 5 except that Compound 2-1 was used instead as the host material of the light-emitting layer.

Example 9

An organic EL device was manufactured in the same manner as that in Example 5 except that Compound 3-1 was used instead as the host material of the light-emitting layer.

Example 10

An organic EL device was manufactured in the same manner as that in Example 5 except that Compound 3-11 was used instead as the host material of the light-emitting layer.

Example 11

An organic EL device was manufactured in the same manner as that in Example 5 except that Compound 3-18 was used instead as the host material of the light-emitting layer.

Example 12

An organic EL device was manufactured in the same manner as that in Example 5 except that Compound 3-22 was used instead as the host material of the light-emitting layer.

Comparative Example 1

An organic EL device was manufactured in the same manner as that in Example 1 except that CBP was used instead as the host material of the light-emitting layer.

Comparative Example 2

An organic EL device was manufactured in the same manner as that in Example 5 except that Compound H-1 below was used instead as the host material of the light-emitting layer.

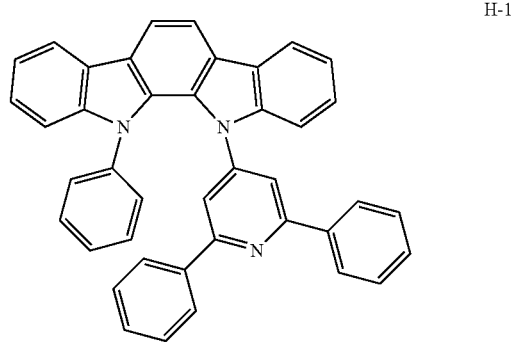 [SMILES: c1ccc(-c2cc(-n3c4ccccc4c4ccc5c6ccccc6n(-c6ccccc6)c5c43)cc(-c3ccccc3)n2)cc1]

H-1

The maximum wavelength of the luminescence spectrum of the organic EL device obtained in each of Examples 5 to 12 and Comparative Examples 1 and 2 is 517 nm, showing that luminescence is provided by Ir(ppy)$_3$. Table 1 shows the luminescence properties of each device.

TABLE 1

| | | Initial properties (@ 10 mA/cm$^2$) | | |
|---|---|---|---|---|
| | Host material | Luminance (cd/m$^2$) | Voltage (V) | Visual luminous efficiency (lm/W) |
| Example 5 | 1-1 | 2790 | 6.0 | 14.6 |
| 6 | 1-19 | 2840 | 6.2 | 14.4 |
| 7 | 1-43 | 2810 | 6.4 | 13.8 |
| 8 | 2-1 | 2840 | 6.5 | 13.7 |
| 9 | 3-1 | 2770 | 6.2 | 14.0 |
| 10 | 3-11 | 2930 | 5.9 | 15.6 |
| 11 | 3-18 | 2820 | 6.3 | 14.1 |
| 12 | 3-22 | 2760 | 6.3 | 13.8 |
| Comparative Example 1 | CBP | 2250 | 9.2 | 7.7 |
| 2 | H-1 | 2740 | 6.7 | 12.8 |

Example 13

On a glass substrate on which indium tin oxide (ITO) had been formed into an anode having a film thickness of 110 nm, each thin film was laminated by using a vacuum deposition method at a vacuum degree of 2.0×10$^{-5}$ Pa. First, on the ITO film, copper phthalocyanine (CuPc) was formed into a film having a thickness of 25 nm as a hole-injecting layer. Next, N,N-di(naphthalen-1-yl)-N,N-diphenyl-benzidene (NPB) was formed into a film having a thickness of 90 nm as a hole-transporting layer. Next, on the hole-transporting layer, co-vapor deposition was carried out by using Compound 3-1 as a host material for a light-emitting layer and an iridium complex [iridium (III) bis(4,6-di-fluorophenyl)-pyridinato-N,C2']picolinate] (Flrpic) which is a blue phosphorescent material as a dopant from different vapor deposition sources, forming a light-emitting layer having a thickness of 30 nm. The concentration of Flrpic was 10%. Next, Alq3 was formed into a film having a thickness of 30 nm as an electron-transporting layer. Further, on the electron-transporting layer, lithium fluoride (LiF) was formed into a film having a thickness of 1.0 nm as an electron-injecting layer. Finally, on the electron-injecting layer, aluminum (Al) was formed into a film having a thickness of 70 nm as an electrode. The resultant organic EL device has a layer structure having an additional electron-injecting layer between a cathode and an electron-transporting layer in the organic EL device shown in FIG. 1.

An external power source was connected to the resultant organic EL device, followed by application of a DC voltage. As a result, the organic EL device was found to have the luminescence properties shown in Table 2. In Table 2, the values of luminance, voltage, and luminous efficiency are those at 2.5 mA/cm$^2$. It should be noted that the maximum wavelength of the luminescence spectrum of the device is 475 nm, showing that luminescence is provided by Flrpic.

Example 14

An organic EL device was manufactured in the same manner as that in Example 13 except that Compound 3-11 was used instead as the host material of the light-emitting layer.

Example 15

An organic EL device was manufactured in the same manner as that in Example 13 except that Compound 3-18 was used instead as the host material of the light-emitting layer.

Example 16

An organic EL device was manufactured in the same manner as that in Example 13 except that Compound 3-22 was used instead as the host material of the light-emitting layer.

Comparative Example 3

An organic EL device was manufactured in the same manner as that in Example 13 except that CBP was used instead as the host material of the light-emitting layer.

Comparative Example 4

An organic EL device was manufactured in the same manner as that in Example 13 except that H-1 was used instead as the host material of the light-emitting layer.

The maximum wavelength of the luminescence spectrum of the organic EL device obtained in each of Examples 13 to 16 and Comparative Examples 3 and 4 is 475 nm, showing that luminescence is provided by Flrpic. Table 2 shows the luminescence properties of each device.

TABLE 2

| | | Initial properties (@ 2.5 mA/cm$^2$) | | |
|---|---|---|---|---|
| | Host material | Luminance (cd/m$^2$) | Voltage (V) | Visual luminous efficiency (lm/W) |
| Example 13 | 3-1 | 140 | 7.5 | 2.3 |
| 14 | 3-11 | 135 | 7.3 | 2.3 |
| 15 | 3-18 | 140 | 7.2 | 2.4 |
| 16 | 3-22 | 120 | 7.4 | 2.0 |
| Comparative Example 3 | CBP | 90 | 8.5 | 1.3 |
| 4 | H-1 | 55 | 8.1 | 0.9 |

As seen from Table 2 as well, the organic EL device of each example exhibits satisfactory luminescence properties as compared to the organic EL device of each comparative example, which suggests the superiority of the present invention.

Industrial Applicability

The material for a phosphorescent light-emitting device of the present invention has the feature that a nitrogen atom of an indolocarbazole skeleton is substituted with pyridine and further substituted with an aromatic ring. In particular, the substitution of pyridine at positions 2 and 6 with an indolocarbazole skeleton and an aromatic ring, respectively, is estimated to improve molecular stability. The above-mentioned material for a phosphorescent light-emitting device is estimated to exhibit satisfactory charge-injecting/transporting properties and to have high durability. The organic EL device using the material has a low driving voltage of the device. In particular, when the organic EL device includes this material for a phosphorescent light-emitting device in a light-emitting layer, it is estimated that the balance between charges improves, and hence the probability of their recombination increases. Further, it is estimated that the material for a phosphorescent light-emitting device has energy in the minimum excited triplet state, the energy being sufficiently high to confine energy in the minimum excited triplet state of a dopant, and thus the transfer of triplet excitation energy from the dopant to a host molecule can be effectively suppressed. By virtue of the above-mentioned respects, high luminous efficiency has been accomplished. In addition, the material for a phosphorescent light-emitting device exhibits a good amorphous characteristic and high thermal stability and has electrochemical stability, resulting in the achievement of an organic EL devise having a long operation life and having high durability.

The organic EL device according to the present invention has practically satisfactory levels in luminescence properties, operation life, and durability. Thus, the organic EL device has a large technical value in applications to flat panel displays (display devices for portable phones, in-vehicle display devices, display devices for OA computers, televisions, and the like), light sources exerting characteristics of planar light emitters (light sources in lighting equipment and copiers and backlight sources in liquid crystal displays and instruments), signboards, sign lamps, and the like.

The invention claimed is:

1. A material for a phosphorescent light-emitting device, comprising an indolocarbazole compound represented by the following general formula (2):

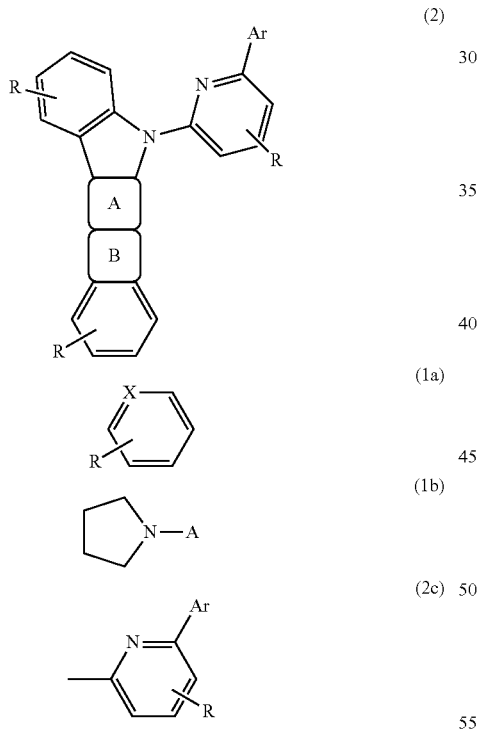

in the general formula (2): a ring A represents an aromatic ring represented by the formula (1a) to be fused with an adjacent ring; and a ring B represents a heterocycle represented by the formula (1b) to be fused with an adjacent ring;
in the formula (1a), X represents a methine group;
in the formula (1b), A represents an aromatic hydrocarbon group having 6 to 38 carbon atoms, an alkyl group having 1 to 10 carbon atoms, a cycloalkyl group having 3 to 11 carbon atoms, or an aromatic heterocyclic group represented by the formula (2c);

in the general formulae (2) and (2c), Ar's each independently represent an aromatic hydrocarbon group having 6 to 18 carbon atoms or an aromatic heterocyclic group having 3 to 17 carbon atoms; and in the general formulae (2), (1a), and (2c), R's each independently represent a hydrogen atom, an alkyl group having 1 to 10 carbon atoms, or a cycloalkyl group having 3 to 11 carbon atoms.

2. A material for a phosphorescent light-emitting device according to claim 1, wherein A in the general formula (2) represents an aromatic hydrocarbon group having 6 to 38 carbon atoms except a fused ring structure or an aromatic heterocyclic group represented by the formula (2c).

3. A material for a phosphorescent light-emitting device according to claim 1, wherein Ar in the general formula (2) represents an aromatic hydrocarbon group having 6 to 18 carbon atoms except a fused ring structure or an aromatic heterocyclic group having 3 to 17 carbon atoms.

4. A material for a phosphorescent light-emitting device according to claim 1, wherein the indolocarbazole compound represented by the general formula (2) comprises an indolocarbazole compound represented by any one of the general formulae (3) to (6):

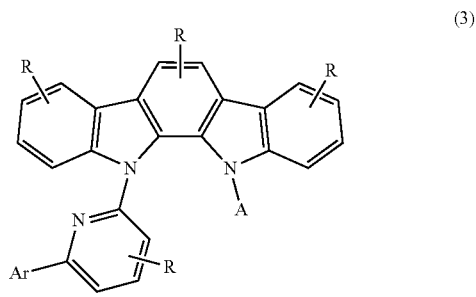

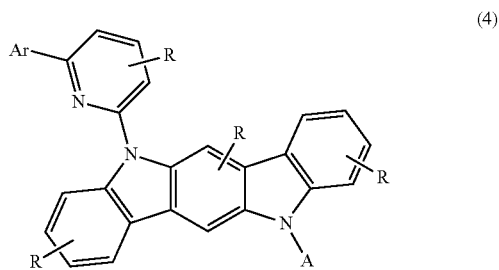

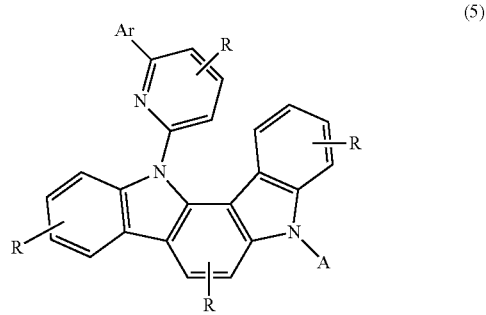

-continued

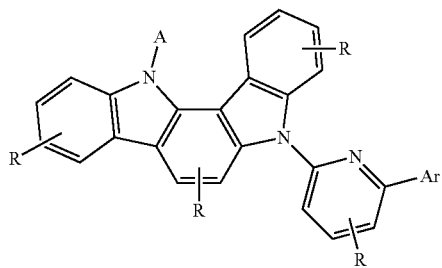

(6)

in the general formulae (3) to (6), A's, Ar's, and R's have the same meanings as those in the general formula (2).

5. An organic electroluminescent device, comprising an anode, an organic layer, and a cathode laminated on a substrate, wherein the organic electroluminescent device comprises an organic layer containing the material for a phosphorescent light-emitting device according to any one of claims 1 to 4.

6. An organic electroluminescent device according to claim 5, wherein the organic layer containing the material for a phosphorescent light-emitting device comprises at least one layer selected from the group consisting of a light-emitting layer, a hole-transporting layer, an electron-transporting layer, and a hole-blocking layer.

7. An organic electroluminescent device according to claim 6, wherein the organic layer containing the material for a phosphorescent light-emitting device comprises a light-emitting layer containing a phosphorescent light-emitting dopant.

* * * * *